(12) United States Patent
Almutairi et al.

(10) Patent No.: US 9,724,417 B2
(45) Date of Patent: *Aug. 8, 2017

(54) NANOCARRIERS WITH MULTI-PHOTON RESPONSE ELEMENTS

(71) Applicant: The Regents of the University of California, Oakland, CA (US)

(72) Inventors: Adah Almutairi, La Jolla, CA (US); Nadezda Fomina, San Diego, CA (US); Jagadis Sankaranarayanan, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 174 days.

This patent is subject to a terminal disclaimer.

(21) Appl. No.: 14/455,613

(22) Filed: Aug. 8, 2014

(65) Prior Publication Data

US 2015/0056181 A1     Feb. 26, 2015

Related U.S. Application Data

(63) Continuation of application No. 13/496,486, filed as application No. PCT/US2010/049996 on Sep. 23, 2010, now Pat. No. 8,828,383.

(60) Provisional application No. 61/244,886, filed on Sep. 23, 2009.

(51) Int. Cl.

| | |
|---|---|
| *A61K 41/00* | (2006.01) |
| *A61K 9/00* | (2006.01) |
| *A61K 9/06* | (2006.01) |
| *A61K 9/51* | (2006.01) |
| *A61K 39/245* | (2006.01) |
| *A61K 39/385* | (2006.01) |
| *A61K 47/34* | (2017.01) |
| *C08G 63/06* | (2006.01) |
| *C08G 63/18* | (2006.01) |
| *C08G 63/91* | (2006.01) |
| *A61K 38/43* | (2006.01) |
| *C07K 16/00* | (2006.01) |
| *C12N 7/00* | (2006.01) |
| *A61K 39/12* | (2006.01) |
| *A61K 39/00* | (2006.01) |
| *A61K 48/00* | (2006.01) |

(52) U.S. Cl.
CPC .......... *A61K 41/008* (2013.01); *A61K 9/0009* (2013.01); *A61K 9/06* (2013.01); *A61K 9/5138* (2013.01); *A61K 9/5146* (2013.01); *A61K 38/43* (2013.01); *A61K 39/12* (2013.01); *A61K 39/245* (2013.01); *A61K 39/385* (2013.01); *A61K 41/0042* (2013.01); *A61K 47/34* (2013.01); *C07K 16/00* (2013.01); *C08G 63/06* (2013.01); *C08G 63/18* (2013.01); *C08G 63/912* (2013.01); *C12N 7/00* (2013.01); *A61K 48/00* (2013.01); *A61K 2039/505* (2013.01); *A61K 2039/5252* (2013.01); *A61K 2039/53* (2013.01); *A61K 2039/55505* (2013.01); *A61K 2039/55572* (2013.01); *A61K 2039/622* (2013.01); *C12N 2710/16634* (2013.01)

(58) Field of Classification Search
None
See application file for complete search history.

(56) References Cited

U.S. PATENT DOCUMENTS

| | | | | |
|---|---|---|---|---|
| 5,643,764 | A * | 7/1997 | Kosak ...................... | C12Q 1/68 435/174 |
| 5,716,982 | A * | 2/1998 | Han ...................... | C07D 311/14 514/263.37 |
| 6,471,968 | B1 | 10/2002 | Baker, Jr. et al. | |
| 7,018,624 | B2 | 3/2006 | Harris | |
| 8,758,778 | B2 | 6/2014 | Almutairi et al. | |
| 8,828,383 | B2 | 9/2014 | Almutairi et al. | |
| 2005/0271615 | A1* | 12/2005 | Shabat .............. | A61K 47/48961 424/78.3 |
| 2006/0069230 | A1 | 3/2006 | Papisov | |
| 2006/0269480 | A1 | 11/2006 | Amir et al. | |
| 2007/0009980 | A1 | 1/2007 | Graham et al. | |
| 2009/0233359 | A1 | 9/2009 | Kwon | |

FOREIGN PATENT DOCUMENTS

WO     2004019993 A1     3/2004

OTHER PUBLICATIONS

Wilson, D.S. et al., "Orally delivered thioketal nanoparticles loaded with TNF-α-siRNA target inflammation and inhibit gene expression in the intestines", 2009, Nature Materials, pp. 923-928.
Alexis, F., et al., "HER-2-Targeted Nanoparticle-Affibody Bioconjugates for Cancer Therapy", 2008, Cem MedChem, pp. 1839-1843.
Xu, L., et al, "Effects of Temperature and pH on the Degradation of Poly(lactic acid) Brushes", 2011, Macromolecules, pp. 4777-4782.
Andersson, L., et al., "Poly(ethylene glycol)-Poly(ester-carbonate) Block Copolymers Carrying PEG-Peptidyl-Doxorubicin Pendant Side Chains: Synthesis and Evaluation as Anticancer Conjugates", 2005, Biomacromolecules, pp. 914-926.
Sankaranarayanan, J., et al., "Multiresponse Strategies to Modulate Burst Degradation and Release from Nanoparticles", 90/90/2010, ACS Nano, pp. 5930-5936.
Mahmoud, E.A., et al., "Inflammation Responsive Logic Gate Nanoparticles for the Delivery of Proteins", 2011, Bioconjugate Chem., 22, pp. 1416-1421.

(Continued)

*Primary Examiner* — Jake Vu
(74) *Attorney, Agent, or Firm* — Eleanor Musick; Musick Davison LLP

(57) ABSTRACT

Compositions are provided in which dendrimers and/or nanoparticles are synthesized with multi-photon responsive elements and self-immolative oligomers. The compositions may be utilized to selectively deliver Payloads within tissue by irradiating the compositions. The compositions may also be used to amplify sensitivity to irradiation.

18 Claims, 19 Drawing Sheets

(56) References Cited

OTHER PUBLICATIONS

Fomina, N., et al., "UV and Near-IR triggered release from polymeric nanoparticles", Jul. 21, 2010, J Am Chem Soc., 132(28): 9540-9542.

Huotari, J., et al., "Endosome Maturation", 2011, The EMBO Journal, (30) 3481-3500.

Sagi, A., et al., "Self-Immolative Polymers", 2008, J. Am Chem Soc., 130(16): 5434-5435.

Kneipp, J., et al., "Two-photon vibrational spectroscopy for biosciences based on surface-enhanced hyper-Raman scattering", 2006, PNAS, (103(46): 17149-17153.

Furuta, T., et al., "Brominated 7-hydroxycoumarin-4-ymethyls: Photolabile protecting groups with biologically useful cross-sections for two photon photolysis", 1999, PNAS vol. 96, pp. 1193-1200.

Gil, P.R., et al., "Composite Nanoparticles Take Aim at Cancer", 2008, ACS Nano, 2(11):2200-2205.

Amir, R.J., et al., "Prodrug Activation Gated by a Molecular "OR" Logic Trigger", 2005, Angew. Chem. Int. Ed., vol. 44, pp. 2-4.

Flomenbom, O., et al., "Some new aspects of dendrimer applications", 2005, J. Luminescence, vol. 111, pp. 315-325.

Bedard, M. F., et al., "Polymeric microcapsules with light responsive properties of encapsulation and release", 2010, Advances in Colloid and Interface Science, vol. 158, pp. 2-14.

Bedard, M.F., et al., "Toward Self-Assembly of Nanoparticles on Polymeric Microshells: Near-IR Release and Permeability", 2008, ACS Nano; 2(9): 1807-1816.

Medina, S.H., et al., "Dendrimers as Carriers for Delivery of Chemotherapeutic Agents", 2009, Chem. Rev., 109, pp. 3141-3157.

Singh, S.K., et al., "Dendrimer a versatile polymer in drug discovery", 2009, Asian J Pharm., 3:178-187.

Sopczynski, B.P., "A New Anti-Tumor Drug Delivery System: Dendrimers", 2008, MMG 445 Basic Biotechnology eJournal, 2:87-92.

Weinstain, R., et al., "Self-Immolative Comb-Polymers: Multiple-Release of Side-Reporters by a Single Stimulus Event", 2008, Chem. Eur. J., 14:6857-6861.

Crampton, H.L., et al., "Dendrimers as drug delivery vehicles: non-covalent interactions of bioactive compounds with dendrimers", Mar. 2, 2007, Polym. Int., 56(4): 489-496.

\* cited by examiner

A                                    B

NANOCARRIERS WITH MULTI-PHOTON
RESPONSE ELEMENTS

RELATED APPLICATIONS

This is a continuation of application Ser. No. 13/496,486, filed Jun. 28, 2012, which is a U.S. National Stage filing of International Application No. PCT/US2010/049996, filed Sep. 23, 2010, which claims priority to U.S. Provisional Application No. 61/244,886, filed on Sep. 23, 2009.

GOVERNMENT RIGHTS

This invention was made with government support under Grant OD006499 awarded by National Institutes of Health. The government has certain rights in the invention.

FIELD OF THE INVENTION

The present invention relates to a method for non-invasively inducing multi-photon processes and releasing compounds of interest to localized areas in living systems.

BACKGROUND OF THE INVENTION

The emerging technology of nanoparticle packaging offers a way to package and deliver compounds of interest that offers significant advantages, in some cases, to delivering certain types of payloads, such as pharmaceuticals, antibodies, and labeling compounds. Many pharmaceutical agents are vulnerable to a reduction in efficacy due to solubility and bioavailability problems. Nanoparticle packaging offers a way to improve their effectiveness. By the appropriate design of nanoparticles, the serum stability of pharmaceutical agents can be enhanced and solubility limitations bypassed.

Nanoparticles also offer the potential, at least, for targeted delivery of their payloads to areas of specific interest. Frequently, an affinity reagent, such as an antibody attached externally to the nanoparticle, is used to direct the nanoparticle to its intended location. A wide variety of nanoparticles are currently available and/or under development. One particular type of nanoparticle is the dendrimer (see, e.g., Cheng, Y., J. Wang, T. Rao, X. He, T. Xu, T.; "Pharmaceutical applications of dendrimers: promising nanocarriers for drug delivery"; Front. Biosci. 13 (2008) 1447-1471.)

Commercially available dendrimers include polyamidoamine ("PAMAM") dendrimers and polypropylene imine ("PPI") dendrimers. Some representative examples of dendrimers and their uses are disclosed in U.S. Pat. Nos. 6,579,906, 6,570,031, 6,545,101, 6,506,218, 6,464,971, 6,452,053, 6,410,680, 6,395,257, 6,365,562, 6,306,991, 6,288,253, 6,228,978, 6,224,898, 6,187,897, 6,184,313, 6,113,946, 6,083,708, 6,068,835, 5,990,089, 5,938,934, 5,902,863, 5,788,989, 5,736,346, 5,714,166, 5,661,025, 5,648,186, 5,393,797, 5,393,795, 5,332,640, 5,266,106, 5,256,516, 5,256,193, 5,098,475, 4,938,885 and 4,694,064.

Forming dendrimers into nanoparticles and/or microparticles, however, does not fully address the question of bioavailability of substances carried by the dendrimers. With the rapid progress of nanotechnology over the past decade, there is growing interest in polymeric biomaterials that can be remotely disassembled in a controlled fashion with an external stimulus, but are otherwise stable under physiological conditions (Wang, W.; Alexander, C. Angew. Chem. Int. Ed., 2008, 47, 7804-7806). Various internal and external stimuli, such as pH, specific enzymes, temperature, and ultrasound are being explored as release mechanisms. (See, e.g., Murthy, N. X., M.; Schuck, S.; Kunisawa, J.; Shastri, N.; Frechet, J. M. J. Proc. Natl. Acad. Sci. U.S.A., 2003, 100, 4995-5000; Veronese, F. M. S., O.; Pasut, G.; Mendichi, R.; Andersson, L.; Tsirk, A.; Ford, J.; Wu, G.; Kneller, S.; Davies, J.; Duncan, R., Bioconjugate Chem., 2005, 16, 775-784; Chung, J. E. Y., M.; Yamato, M.; Aoyagi, T.; Sakurai, Y.; Okano, T. J. J., Controlled Release, 1999, 62, 115-127; Liu, S. Q.; Tong, Y. W.; Yang, Y. Y., Biomaterials, 2005, 26, 5064-5074; Na, K.; Lee, K. H.; Lee, D. H.; Bae, Y. H., Eur. J. Pharm. Sci., 2006, 27, 115-122; Gao, Z. G.; Fain, H. D.; Rapoport, N. J., Controlled Release, 2005, 102, 203-222; Nelson, J. L.; Roeder, B. L.; Carmen, J. C.; Roloff, F.; and Pitt, W. G. Cancer Research 2002, 62, 7280-7283).

One of these promising approaches is the use of light to trigger the remote disassembly of polymers (Goodwin, A. P.; Mynar, J. L.; Ma, Y. Z.; Fleming, G. R.; Frechet, J. M. J. J. Am. Chem. Soc. 2005, 127, 9952-9953). Light stimulus is especially attractive as it can be remotely applied for a short period of time with high spatial and temporal precision. Some forms of light, such as near-infrared (NIR) light, can penetrate deep into tissue and thus potentially have many in vivo applications (see, e.g., Near-Infrared Applications in Biolechnology; Raghavachari, R., Ed.; Practical Spectroscopy Series 25; Marcel Dekker: New York. 2001).

Two-photon excitation microscopy, for example, has been used as an alternative to confocal and deconvolution microscopy that provides distinct advantages for three-dimensional imaging. In particular, two-photon excitation excels at imaging of living cells, especially within intact tissues such as brain slices, embryos, intact organs, and even entire animals. Two-photon excitation microscopy provides superior optical sectioning at greater depths in thick specimens than is possible by other methods. This ability to see within tissues demonstrates the practicality of using two-photon technology for other purposes within a tissue and/or organism.

Three-photon excitation is a related non-linear optical absorption event that can occur in a manner similar to two-photon excitation. The difference is that three photons must interact simultaneously with the fluorophore to illicit a transition to the excited singlet state. A benefit of three-photon excitation is that successful absorption requires only a tenfold greater concentration of photons than two-photon absorption, making this technique attractive for some experiments.

Multi-photon phenomena allow unparalleled spatio-temporal control, and where longer wavelengths are employed, also allow deeper penetration into turbid bulk media such as tissue. Despite the revolutionary impact these phenomena have had on neuroscience, microscopy and lithography, it has been generally very difficult to apply this technique in vivo to stimulate and/or deliver biomaterials, diagnostics, and/or drugs. The technology for fully exploiting these advantages has lagged behind and there is still an unmet need for biomaterials that can efficiently respond to light, especially NIR light. No robust systems currently exist for in vivo use of multi-photon-responsive materials to deliver Payloads of interest.

BRIEF SUMMARY OF THE INVENTION

In one aspect, the present invention features a composition that comprises a multi-photon responsive element covalently linked to a self-immolative backbone subunit. In various embodiments of this aspect, the multi-photon responsive element is a two-photon responsive element; non-limiting examples of which can be drawn from the bromo-coumarin group, and other examples are described herein. In some embodiments of this aspect, the composition further comprises a molecular network, and may further comprise a Payload. In various embodiments, the molecular network may comprise acrylamide elements and/or PEG elements. In some embodiments the self-immolative backbone subunit is a self-immolative dendrimer oligomer, and/or may comprise an assembled dendritic structure. Various possible self-immolative backbone subunits are described herein.

In another aspect, the present invention features a kit containing a composition of the invention.

In an additional aspect, the present invention features a method of delivering a Payload to a tissue, or a selected position, wherein a composition of the invention as described herein, wherein that composition comprises a Payload, is delivered to a tissue, or a selected position, and irradiated with an appropriate wavelength of electromagnetic radiation, e.g., light, so as to activate the multi-photon responsive element, which in turn disrupts the composition of the invention in the selected tissue or in the selected location, thereby releasing the Payload. In some embodiments, the radiation used is near infrared light, in other embodiments it may be UV light. In various aspects of the invention, the Payload may comprise a pharmaceutical agent, stem cell differentiation factors, immunogens, and/or antibodies.

In a further aspect, the present invention features a method for amplifying sensitivity to electromagnetic radiation, or light, such as UV light or near infrared light. In some embodiments, this aspect features a composition that comprises a multi-photon responsive element and a self-immolative backbone. In some embodiments of this aspect, this composition further features a molecular network, and may also feature a payload. In this aspect, the composition is then irradiated with electromagnetic radiation, triggering the multi-photon responsive element together with the self-immolative backbone. In some embodiments that also have a molecular network and/or a Payload, this will disrupt the molecular network and/or release the Payload.

In still another aspect, the present invention features a method of manufacturing a composition of the invention as described herein.

BRIEF DESCRIPTION OF THE DRAWINGS

In FIG. 25a, the NMR profile of a multi-photon responsive element+crosslinker is depicted. FIGS. 25b and 25c show the crosslinker after the multi-photon reaction followed by NMR and UV-Vis, respectively.

FIG. 27b is a graph of cell viability using the MTT-toxicity assay.

DETAILED DESCRIPTION OF THE EXEMPLARY EMBODIMENTS

Figure 1:
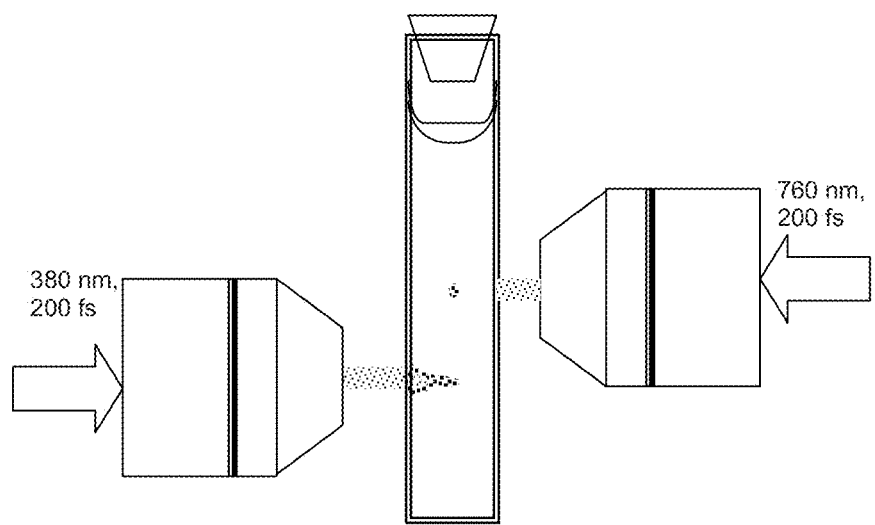
FIG. 1 illustrates an experimental set-up for demonstrating the high spatial and temporal resolution of multi-photon excitation (MPE). This photograph shows fluorescence of a dye following one photon (above) and two-photon (below) excitation. Spatial and temporal stimuli control may be realized by using two-photon radiation capable of penetrating bulk turbid media to a desired depth. Two-photon absorption (2PA) offers unparalleled 3D spatial and temporal control (Denk, W., Strickler, J. H. & Webb, W. W., 2-Photon Laser Scanning Fluorescence Microscopy, *Science* 248, 73-76 (1990)). Using two intersecting beams of near infrared (NIR) laser light, pinpoint accuracy can be achieved. Activation will occur only in regions of high NIR light intensity where the two beams cross, and does not happen outside the two beams to an appreciable degree.

Various embodiments of the present invention provide methods, compounds and formulations for packaging compounds and/or other substances (e.g., Payloads) and for optical activation and/or release of these Payloads. In some embodiments of the present invention, methods, compounds, and formulations are used inside tissues and living organisms non-invasively, with a previously unattainable control of depth and location. Some embodiments of the present invention also allow for the amplification of multi-photon driven processes so that a single multi-photon absorption event may produce multiple events in response, again with the ability to do so non-invasively and with a previously unattainable control of depth and location within turbid media such as tissue. Such amplification may, for example, greatly increase a practitioner's ability to conduct an assay within a tissue. The potential of the embodiments of the invention is large and broad, allowing previously invasive procedures to be performed non-invasively, and previously inaccessible target sites to be accessed specifically and precisely for purposes such as treatment and/or diagnosis.

Some embodiments of the present invention provide polymers that are capable of providing an amplified response to multi-photon irradiation. A multi-photon responsive moiety is repetitively embedded in a polymer during or after the synthesis of that polymer. The polymer with the multi-photon responsive element may in turn be used in the formation of materials, nanoparticles, and/or microparticles. When that multi-photon responsive moiety simultaneously absorbs, for example, two photons, changes in that molecular moiety disintegrate the polymer and can consequently cause a domino effect that unravels the entire material, nanoparticle, and/or microparticle. It is similar to a net where the cross-linking strands can be selectively removed from a distance, allowing what was trapped within the net to escape from the surviving strands that can no longer, by themselves, enclose the former cargo. Thus, when multi-photon responsive moieties are incorporated into materials, nanoparticles and/or microparticles during their synthesis it establishes sensitivity to multi-photon light stimulation, and this, in turn, allows the facile triggering of the fragmentation of the materials, nanoparticles and/or microparticles at selected target sites.

Many embodiments of the present invention also incorporate self-immolative oligomers into the structure of the materials, nanoparticles and/or microparticles formed and used according to the present invention. These self-immolative oligomers are frequently linked, either directly or through other self-immolative oligomers, to the multi-photon responsive elements. Thus, when the multi-photon responsive element is triggered via the absorption of radiation, this in turn may activate changes to the self-immolative oligomers.

Some embodiments of the present invention provide the ability to activate processes through turbid media, such as within an organism, non-invasively with a previously unattainable control of depth and location. This takes advantage of the ability of some forms of light, such as near infrared red light, to penetrate turbid media such as tissue. In such embodiments of the present invention, when a multi-photon responsive element, repetitively built into the very structure of a material, nanoparticle and/or microparticle, simultaneously absorbs multi-photon irradiation from an appropriate light source, this activates changes in that multi-photon responsive element that disrupts the structure of that material, nanoparticle and/or microparticle causing it to virtually disintegrate at a precise time and location chosen by the practitioner. This process may in turn activate the Payload (e.g., changing the fluorescence profile of a Payload comprising a fluorescent molecule), or may allow the Payload to activate a process taking place at the point of release (e.g., a Payload comprising an enzyme now capable of cleaving nearby substrates).

Some embodiments of the present invention provide an ability to produce an amplified response to multi-photon-driven processes, such amplified responses may be produced non-invasively, even beneath bulk turbid media, such as within the tissue of a living organism. Triggering the multi-photon responsive elements, with appropriate radiation, that are attached to self-immolative crosslinkers where both are incorporated into materials and/or polymers amplifies (or creates) their collective sensitivity to light and allows for highly sensitive triggered fragmentation at target sites. Materials and/or polymers that comprise such self-immolative crosslinkers together with multi-photon responsive elements may in turn comprise part of nanoparticles and/or microparticles.

Some embodiments of the present invention provide self-immolative oligomer and self-immolative oligomer strategies. Such oligomers and/or strategies may be used in embodiments of the present invention to create higher order molecular assemblies (bulk materials, nanoparticles and/or microparticles) with extreme sensitivity towards multi-photon irradiation. A single event—the cleavage of the triggering group—gives rise to multiple cleavages leading to significant disruption of the structure, thus delivering the Payload at the time and location of the practitioner's choosing. Thus, embodiments of the present invention enable previously unattainable optical remote control and/or activation of materials, substances and processes.

Figure 10:
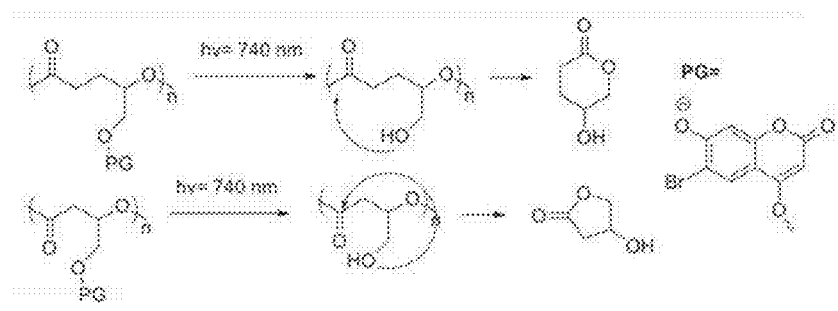
FIG. 10 is a diagram representing the structures of polyester compounds that unravel and fragment completely when one of the hydroxyl protecting groups is cleaved by two-photon absorption.
Figure 11:
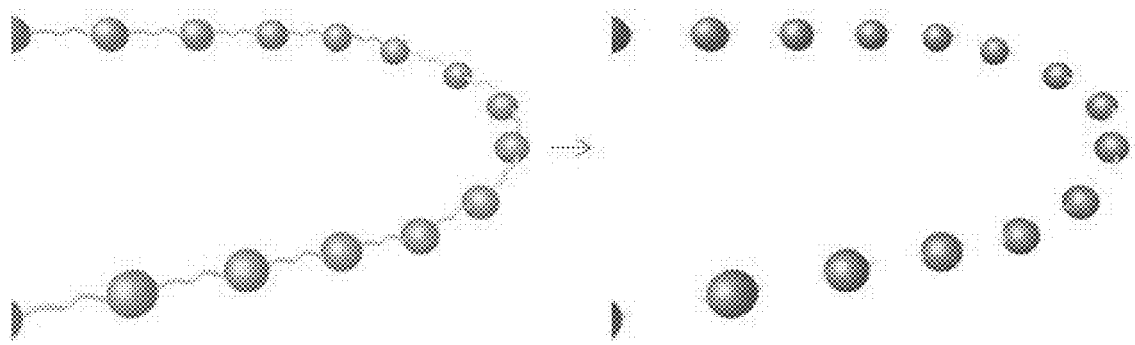
FIG. 11 is a diagram representing a polymer strand (left) and its complete fragmentation (right).
Figure 12:
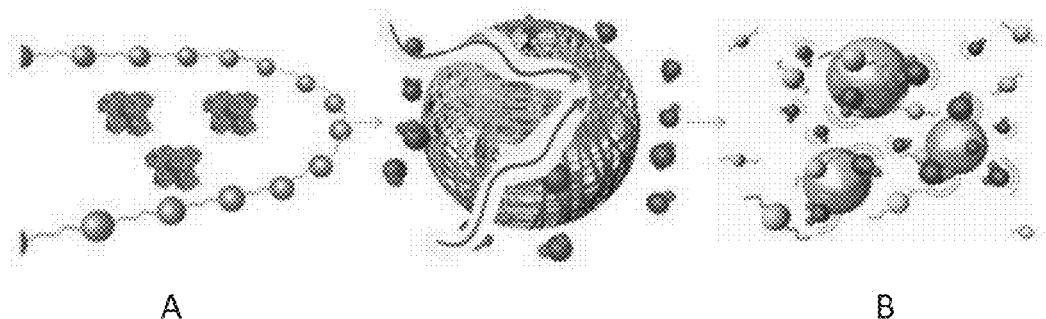
FIG. 12A is a diagram representing emulsion condensation methods that can be used to form nanoparticle or microparticles encapsulating a Payload (hydrophilic or hydrophobic).
FIG. 12B represents a multi-photon responsive nanoparticle made from polymer strands that encapsulate a Payload and then unravel when directed by irradiation with two-photon light. This concept may be thought of as an optical nanosyringe, capable of releasing a high concentration of Payload when and where directed by a practitioner.

FIG. 10 illustrates examples of some polyesters that will unravel and fragment completely when one of the hydroxyl protecting groups is cleaved by two-photon absorption.

Novel self-immolative oligomers, by themselves, may also be featured as embodiments of the present invention.

Materials, nanoparticles, and/or microparticles synthesized according to the instant invention may incorporate only self-immolative oligomers described in the present invention, or they may incorporate any suitable self-immolative oligomers.

Earlier work using light-activated self-immolative oligomers has been reported. Shabat described use of an ortho-nitrobenzyl group as a light-sensitive trigger in "Self-Immolative Dendrimers" (2003) *Angewandte Chemie-International Edition*, 42, 4494-99.

Figure 2:
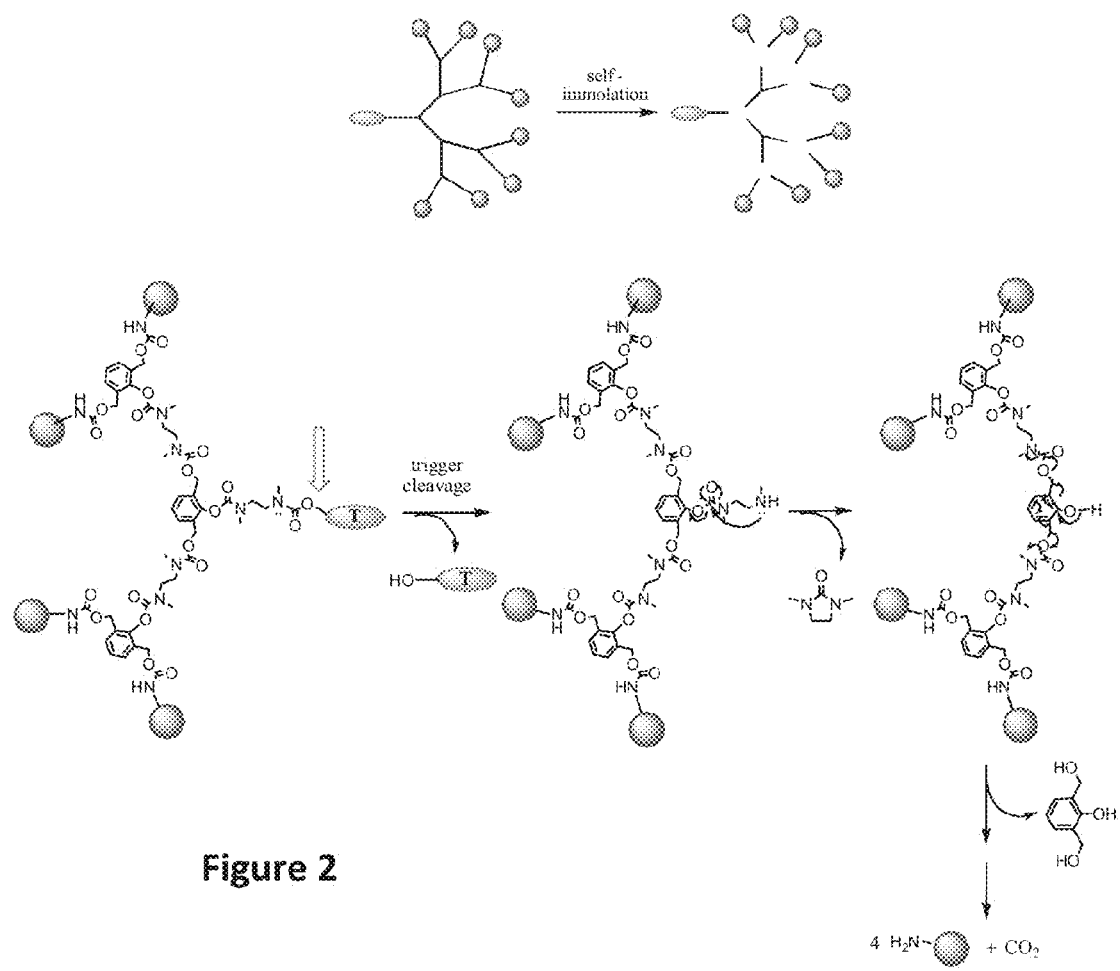
FIG. 2 is a diagram illustrating self-immolative fragmentation of dendrimers where the ovals represent the triggering group and the spheres represent possible Payloads.

Previous work developing self-immolative oligomers, albeit not ones that are light-sensitive, has produced dendritic structures which can be branched (FIG. 2) or linear (FIG. 3) (see, generally, Amir, R. J., Danieli, E. & Shabat, D.; "Receiver-amplifier, self-immolative dendritic device"; (2007) *Chemistry-a European Journal* 13, 812-21; Amir, R. J., Popkov, M., Lerner, R. A., Barbas, C. F. & Shabat, D.; "Prodrug activation gated by a molecular "OR" logic trigger;" (2005) *Angewandte Chemie-International Edition* 44, 4378-81; Amir, R. J. & Shabat, D.; "Self-immolative dendrimer biodegradability by multi-enzymatic triggering"; (2004) *Chemical Communications*, 1614-15; Amir, R. J. & Shabat, D.; "Domino dendrimers" (2006) *Polymer Therapeutics I: Polymers as Drugs, Conjugates and Gene Delivery Systems* 192, 59-94; Weinstain, R., Sagi, A., Karton, N. & Shabat, D.; "Self-immolative comb-polymers: Multiple-release of side-reporters by a single stimulus event"; (2008) *Chemistry-a European Journal* 14, 6857-6861; Sagi, A., Weinstain, R., Karton, N. & Shabat, D.; "Self-immolative polymers"; *J Am Chem. Soc* (2008) 130, 5434; Amir, R. J., Shabat, D; U.S. Patent Publication No. US 2006/0269480). These dendrimers are well-defined synthetic macromolecules characterized by a large number of functional groups. Their well-defined structure distinguishes them from many other classes of nanoparticles and/or microparticles.

Generally speaking, dendrimers are molecules synthesized with repeating units radiating out from a core. Each tier of repeating units is referred as a "generation". This process, which is classified as "convergent" or "divergent", creates highly branched macromolecules emanating from the central core. Divergent dendrimers are synthesized outward from the central core. Dendrimers can be made in a wide variety of sizes and molecular weights, and can include inner cavities that may be exploited to carry molecules of interest. Dendrimers can also be adapted so as to have uniform or discrete functionalities, and can be further adapted with regard to surface moieties, interior moieties, and solvent interactions.

Dendritic macromolecules may also be used for the amplification of the molecular effects following chemical or enzymatic triggering. A second-generation dendrimer (in other words, a dendrimer with two tiers of oligomers) incorporating 2,6-bis(hydroxymethyl)-p-cresol units and carbamate linkages has been synthesized and demonstrated to undergo triggered disassembly (see, e.g., FIG. 2). Cleavage of the triggering group, frequently by means of an enzyme, initiates a spontaneous cyclization to form an N,N'-dimethylurea derivative. The resultant phenol then undergoes a double 1,4-quinone methide rearrangement, followed by spontaneous decarboxylation. The cyclization/rearrangement steps are then repeated to liberate four pyrene reporter molecules. A third-generation self-immolative dendrimer of the same general structure bearing eight 4-nitroaniline reporter molecules was also successfully synthesized. Thus, higher generation self-immolative dendrimers provide higher signal-to output ratio. Consequently, a single event—cleavage of the triggering group—gives rise to multiple outputs, and the signal-to-output ratio may be tuned by controlling the degree of branching.

Thus, in certain embodiments of the present invention, such self-immolative strategies may be used to create higher order molecular assemblies (materials, nanoparticles and microparticles) with enhanced sensitivity towards multi-photon irradiation. A single event—the cleavage of the triggering group—gives rise to multiple cleavages leading to the disintegration of the overall structure with its associated network. Self-immolative crosslinkers used to crosslink the strands of a molecular network facilitate the rapid and controlled disintegration of the molecular network.

In some aspects of the embodiments of the present invention, the structure that incorporates the self-immolative oligomers comprises a dendritic structure.

Some embodiments of the present invention provide methods for synthesizing and utilizing nanoparticles and/or microparticles that include Payload(s) whereby the packaged Payload(s) can be released from the polymeric structure of the nanoparticles and/or microparticles upon receipt of an optical signal, usually a multi-photon stimulation, which causes the self-immolative disruption of the particle's molecular network, thereby releasing the Payload(s). By thus creating a molecular network that can be released remotely using wavelengths of light capable of penetrating tissue, compounds included in the Payload may be activated and/or released non-invasively inside living systems at the practitioner's discretion, with a previously unattainable control of depth and location. The potential of such remote control is large and broad, allowing previously invasive procedures to be performed non-invasively, and previously inaccessible target sites to be reached specifically and precisely for treatment and/or diagnosis.

Embodiments of the present invention provide a broadly-faceted strategy for the delivery of biological agents, i.e., Payload(s), via nanoparticles and/or microparticles involve sequestration or encapsulation the Payload(s) within the nanoparticles and/or microparticles. Before the teachings of the present invention, the types of small particles frequently involved in this approach were nanogels, microgels, nanospheres, microspheres, polymer micelles, and/or polymerized liposomes. In general, retention of the active compound in the nanoparticles was achieved by physical entrapment or by thermodynamic forces such as hydrophobic interactions. The use of microbeads with a slowly degradable shell, consisting of, for example, poly(beta-amino ester)s or poly (ortho ester) is described in the literature (Wang, C., Ge, Q., Ting, D., Nguyen, D., Shen, H.-R. Chen, J., Eisen, H. N., Heller, J., Langer, R. & Putnam, D.; "Molecularly engineered poly(ortho ester) microspheres for enhanced delivery of DNA vaccines"; *Nature Materials* (2004) 3, 190-196). Such microspheres were conveniently prepared from a preformed polymer using a water-oil-water double emulsion method. Similarly, a number of pre-formed hydrophobic polymers are used to encapsulate hydrophobic drugs or hydrophilic macromolecules in processes known as nanoprecipitation and double emulsion condensation (Bilati, U., Allemann, E. & Doelker, E.; "Nanoprecipitation versus emulsion-based techniques for the encapsulation of proteins into biodegradable nanoparticles and process-related stability issues;" *Aaps Pharmscitech* (2005) 6, E594-604). The teachings of the present invention are in contrast to the small particles thus described and improve upon such particles by combining multi-photon responsive units and self-immolative oligomers in defined structures that provide multi-photon control to molecular networks that encapsulate Payload(s).

Some embodiments of the present invention therefore feature selected concepts drawn from self-immolative dendritic structures are combined with unstructured polymers to provide nanoparticles and/or microparticles that that can be dissembled rapidly, but only when triggered by multi-photon irradiation. Some embodiments of the present invention improves upon the construction of self-immolative dendrimers such as those described by Shabat et al. (see supra) by further adding polymers to mechanically entrap multiple copies of molecules within the nanoparticle and/or microparticle, as opposed to each Payload molecule being covalently coupled to a multi-photon responsive moiety.

In some embodiments of the present invention, self-immolative dendritic crosslinkers comprising multi-photon responsive elements are used in the inverse emulsion polymerization of acrylamide to form a molecular network forming nanoparticles and/or microparticles. Such nanoparticles and/or microparticles may also be designed to comprise Payload(s), and may also contain a Payload(s). The final steps of assembly of the nanoparticle in many embodiments may take place in the simultaneous presence of coupled multi-photon responsive elements and self-immolative oligomers, the Payload(s), and the constituents of the molecular network. e.g., acrylamide. It is one advantage of some embodiments of the present invention that the final assembly of the nanoparticle and/or microparticles may take place in conditions that should not denature or otherwise disrupt the Payload(s)'s constituents. It is also an advantage of some embodiments of the present invention that the Payload(s) is not covalently linked to any part of the molecular network in which it is contained.

A significant advantage of the present invention is that reliance on a mechanical entrapment mechanism relieves the practitioner of the need to tailor the chemistry of a selected multi-photon compound to each and every Payload desired. This enables a tremendously versatile strategy for Payload delivery.

In other embodiments of the invention, polymers other than acrylamide can be attached to the self-immolative dendritic crosslinkers and multi-photon responsive elements of the present invention. One such polymer is Acetalated-dextran. Another example of a non-acrylamide network that may be used is polyethylene glycol (PEG).

For some embodiments of the present invention, multi-photon responsive elements with high two-photon action cross sections are preferred, generally about 1 GM (Goeppert-Mayer, GM; 1 GM=10-50 $cm^4 \cdot s$/photon).

Photo protecting groups (PPGs) were originally developed as protecting groups for organic synthesis. Today, however, PPGs span an entire gamut of applications from release of neurotransmitters, ions, drugs, biomolecules like proteins and enzymes[17] to commercial chemicals such as fragrances (Miranda, K. M., Nagasawa, H. T. & Toscano, J. P.; "Donors of HNO"; *Current Topics in Medicinal Chemist*, (2005) 5, 647-664; Pavlos, C. M., Xu, H. & Toscano, J. P. "Photosensitive precursors to nitric oxide"; *Current Topics in Medicinal Chemistry* (2005) 5, 635-645; Specht, A., Ziarelli, F., Bernard, P., Goeldner, M. & Peng, L.; "para-Sulfonated calixarenes used as synthetic receptors for complexing photolabile cholinergic ligand;" *Helvetica Chimica Acta* (2005) 88, 2641-2653; Herrmann, A.; "Controlled release of volatiles under mild reaction conditions: From nature to everyday products"; *Angewandte Chemie-International Edition* (2007) 46, 5836-5863). The choice of which PPG to use depends on the system under consideration, and must be customized to each specific application. There has been extensive research into development of one photon PPGs (OP-PPGs) and in applications of these OP-PPGs to release molecules of interest (Millar, A. G., Zucker, R. S., Ellis-Davies, G. C. R., Charlton, M. P. & Atwood, H. L.; "Calcium sensitivity of neurotransmitter release differs at phasic and tonic synapses;" *Journal of Neuroscience* (2005) 25, 3113-3125; Falvey, D. E. & Sundararajan, C.; "Photoremovable protecting groups based on electron transfer chemistry"; *Photochemical & Photobiological Sciences* (2004) 3, 831-838; Corrie, J. E. T. & Barth, A.; "Decarboxylation is a major pathway in photolysis of caged calcium reagents"; *Biophysical Journal* (2005) 88, 340a-340a). However, developments in two-photon PPGs (TP-PPGs) are still in their infancy. Despite the scarcity of TP-PPGs, their applications are manifold in biological sciences (Furuta, T., Wang, S. S. H., Dantzker, J. L., Dore, T. M., Bybee, W. J., Callaway, E. M., Denk, W. & Tsien, R. Y.; "Brominated 7-hydroxycoumarin-4-ylmethyls: Photolabile protecting groups with biologically useful cross-sections for two photon photolysis"; *Proc.s Natl. Acad. Sci USA* (1999) 96, 1193-200; Tsien, R. Y., Miyawaki, A., Zacharias, D., LevRam, V., Llopis, J., Baird, G., Zlokarnik, G., Li, W. H., Furuta, T. & Dore, T.; "New molecules to peek and poke at signal transduction"; *Journal of General Physiology* (1999) 114, 3A-3A; Aujard, I., Benbrahim, C., Gouget, M., Ruel, O., Baudin, J. B., Neveu, P. & Jullien, L.; "o-Nitrobenzyl photolabile protecting groups with red-shifted absorption: Syntheses and uncaging cross-sections for one- and two-photon excitation"; *Chemistry-a European Journal* (2006) 12, 6865-6879). One attractive aspect of using Near Infrared radiation is its ability to penetrate and propagate deep into turbid media; however, in spite of that prior applications of TP-PPGs have focused on the use in thin layer settings.

One non-limiting example of a near infrared-labile protecting group that can be used in embodiments of the present invention is the bromo-coumarin class; a well-established class of two-photon protecting groups (see, e.g., Furuta, T., Watanabe, T., Tanabe, S., Sakyo, J. & Matsuba, C. Photriggers for nucleobases with improved photochemical properties. *Organic Letters* (2007) 9, 4717-4720). Such compounds have a proven track record of success when used as a two-photon photoremovable protective group in the case of nucleobases (Almutairi, A., Rossin, R., Shokeen, M., Hagooly, A., Ananth, A., Capoccia, B., Guillaudeu, S., Abendschein, D., Anderson, C. J., Welch, M. J. & Frechet, J. M. J.; "Biodegradable dendritic positron-emitting nanoprobes for the noninvasive imaging of angiogenesis"; *Proc. Natl. Acad. Sci. USA* (2009) 106, 685-690) and in the case of uncaging glutamate in brain cells (Almutairi, A., Guillaudcu, S. J., Berezin, M. Y., Achilefu, S. & Frechet, J. M. J.; "Biodegradable pH-sensing dendritic nanoprobes for near-infrared fluorescence lifetime and intensity imaging;" *J Am Chem Soc*; (2008) 130, 444).

Figure 8:
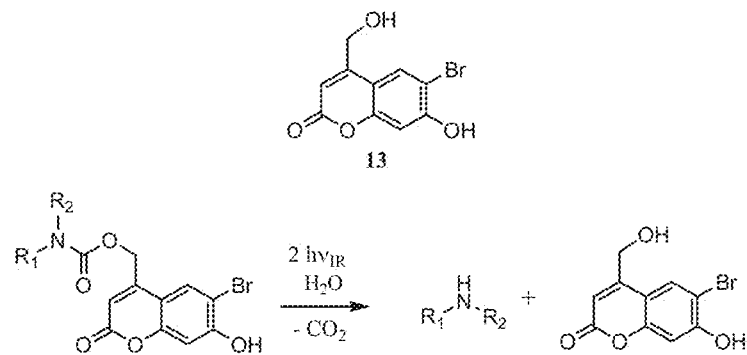
FIG. 8 is a diagram representing the structure of a triggering group for self-immolative crosslinker 1.

Bromo-coumarins have been used synthesize dendritic structures for use with some embodiments of the present invention. When in its carbamate form (FIG. 8), bromo-coumarin has been shown to release amines upon two-photon IR photolysis with a high action cross-section (0.95 GM at 740 nm and 0.37 GM at 800 nm) (Almutairi et al., *J Am Chem. Soc* (2008)).

Figure 9:
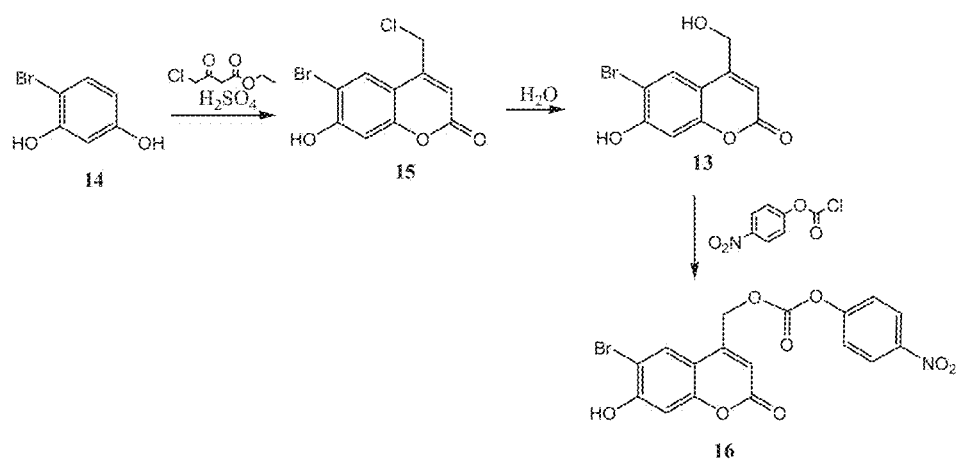
FIG. 9 is a diagram representing the synthesis of a triggering group.

The synthesis of a compound useful as a multi-photon responsive element is depicted in FIG. 9, compound 13. It can be accessed from commercially available 4-bromoresorcinol 14 by reacting it with ethyl 4-chloroacetoacetate to give compound 15. Hydrolysis of 15 will afford the desired compound 13. In order to install the coumarin triggering group onto dendritic crosslinker 1, compound 13 was converted into compound 16 by reacting it with p-nitrophenyl-chloroformate.

A number of other promising two-photon-protecting groups with high action cross-sections (1-6 GM) are currently available that can be used with the present invention (see, e.g., Gug, S., Bolze, F., Specht, A., Bourgogne, C., Goeldner, M. & Nicoud, J. F.; Molecular Engineering of Photoremovable Protecting Groups for Two-Photon Uncaging; *Angewandte Chemie-International Edition* (2008) 47, 9525-9529).

Other two-photon systems with large two-photon-action cross-sections used in neuroscience, fluorescence microscopy, cell biology, and photodynamic therapy have been investigated for the covalent release of biomolecules. In previous studies, however, the molecule of interest (i.e., the Payload(s)) was directly and covalently linked to the structure containing the two-photon moiety.

Embodiments of the present invention improve upon that art by entrapping multiple copies of the Payload(s) within a nanoparticle and/or microparticle by effectively surrounding them with a net built from polymers, but allowing the covalently photo-unraveling of this net at a site and a time of the practitioner's choosing. Because the molecular structure of the molecular network is built upon self-immolative principles, the effect of a single multi-photon absorption event causes the fragmentation of more than one bond, and thus the self-immolative structure amplifies the overall effect of the absorption event.

In some embodiments that use multi-photon responsive moieties, two-photon responsive moieties are used. By requiring multi-photon stimulation, or two-photon stimulation, an added element of control has been added to the system that may require high local intensities at a specific location with negligible release elsewhere.

Figure 4:
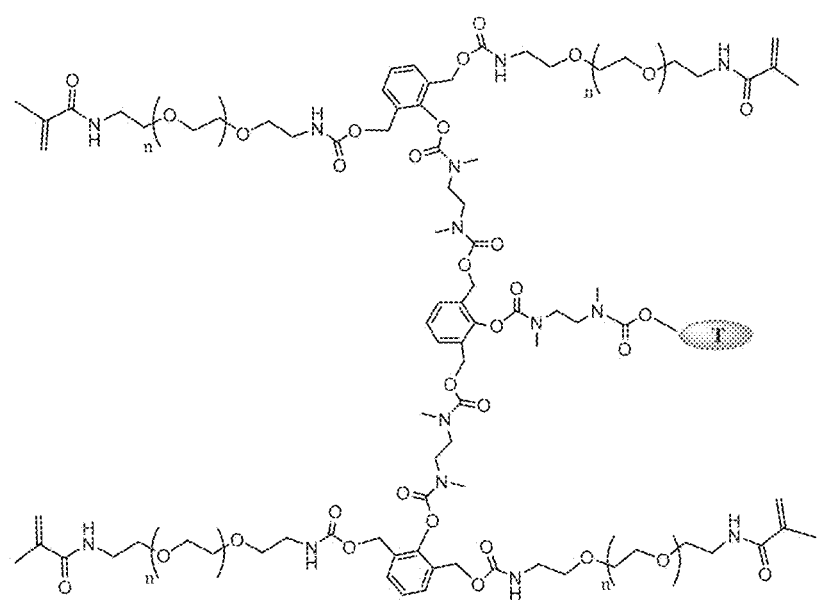
FIG. 4 is a diagram representing the structure of a second generation dendritic self-immolative crosslinker (in other words, a two-tiered dendritic self-immolative crosslinker).

In some embodiments of the present invention, multi-photon responsive elements coupled to self-immolative dendritic crosslinkers, such as the exemplary structure shown in FIG. 4, improve over what existed prior to the present invention. Self-immolative linkers such as shown in FIG. 4 may further be used in the inverse emulsion polymerization of acrylamide (FIG. 5) to form novel nanoparticles and/or microparticles. Thus, the present invention improves upon prior forms of hydrogel nanoparticles (e.g., Cohen, J. A., Beaudette, T. T., Tseng, W. W., Bachelder, E. M., Mende, I., Engleman, E. G. & Frechet, J. M. J. T-Cell Activation by Antigen-Loaded pH-Sensitive Hydrogel Particles in Vivo: The Effect of Particle Size. *Bioconjugate Chemistry* 20, 111-119 (2009); Cohen, J. L., Almutairi, A., Cohen, J. A., Bernstein, M., Brody, S. L., Schuster, D. P. & Frechet, J. M. J. Enhanced cell penetration of acid-degradable particles functionalized with cell-penetrating peptides. *Bioconjugate Chemistry* 19, 876-881 (2008)). In some embodiments of the present invention, acrylamide groups capable of being polymerized are introduced and connected to the core of the crosslinker comprising multi-photon responsive elements and self-immolative crosslinkers through polyethylene glycol ("PEG") chains. The PEG chains may also be modified for improved water solubility and compatibility with inverse emulsion polymerization methods.

Figure 5:
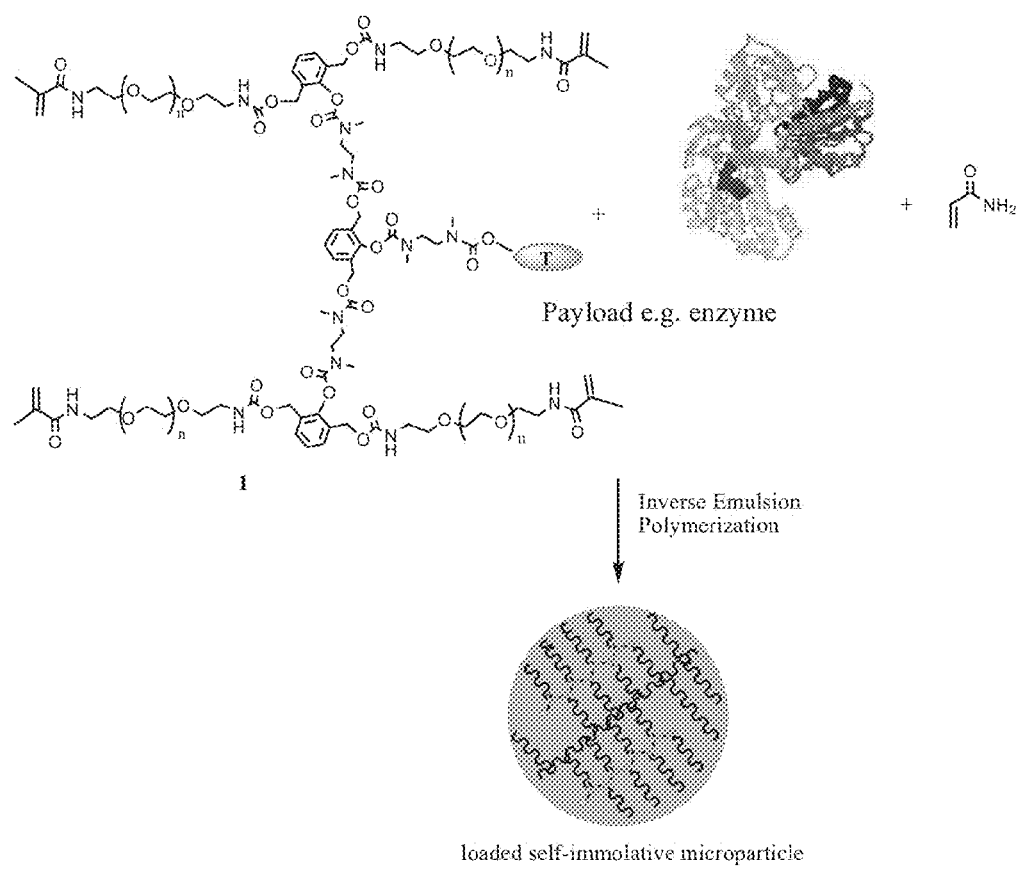
FIG. 5 is a diagram representing inverse emulsion polymerization of acrylamide assembled with self-immolative crosslinker 1 in the presence of a Payload (e.g., enzymes, antibodies, toxins, and/or catalysts etc.) to form loaded nanoparticles.

Referring to FIGS. 4 and 5, inverse emulsion copolymerization of acrylamide and crosslinker 1 functionalized with an acrylamido group in the presence of a water soluble Payload (e.g. an enzyme or an APA) resulted in the formation of self-immolative nanoparticles with an entrapped Payload (FIG. 5).

Figure 6:
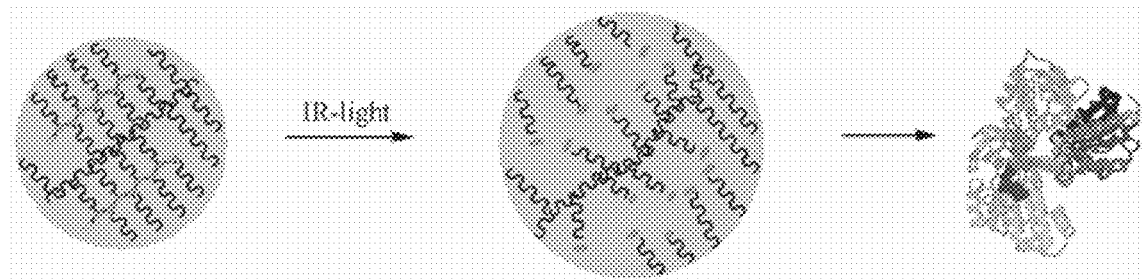
FIG. 6 is a diagram representing the release of Payload triggered by IR-light.

In conventional dendrimers, one triggering event may lead to the cleavage of one bond (signal-to-output ratio equals 1). In some embodiments of the present invention, a single triggering event will lead to the number of cleaved bonds equal to the number of branches in the case of dendritic crosslinker, or to the number of monomer units in the case of linear polymeric crosslinker. Irradiation with IR light may be thus used to trigger widespread fragmentation of the crosslinkers within the microparticle, resulting in "swelling" of the microparticle and subsequent release of its payload (FIG. 6).

Systems, such as those of the present invention, capable of a collective and amplified response have not been heretofore developed utilizing the features of multi-photon response coupled to self-immolative oligomers, together with an ability to facilely package Payloads of interest to a practitioner.

Figure 3:
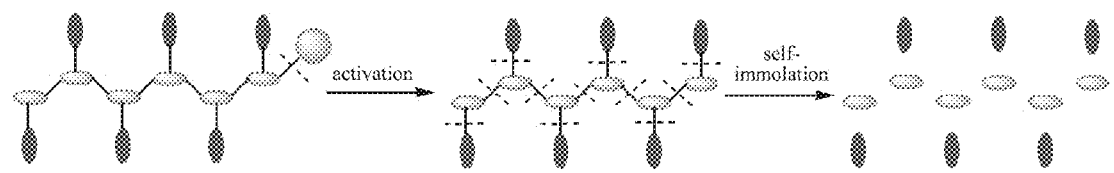
FIG. 3 is a diagram illustrating self-immolative fragmentation of linear oligomers where the spheres represent the triggering group and the vertical ovals represent possible Payloads.

Thus, according to the present invention, procedures are described to provide materials that have an amplified, highly sensitive, response to non-invasive multi-photon irradiation. One approach of the instant invention is to incorporate self-immolative oligomers as crosslinkers into materials, nanoparticles and/or microparticles so as to amplify their sensitivity to light and allow for highly sensitive and triggered fragmentation at targeted sites. When multi-photon responsive elements are incorporated, together with self-immolative oligomers, within a material, nanoparticle and/or microparticle in a specific manner, they can initiate a cascade of changes within the material, nanoparticle and/or microparticle when triggered by appropriate irradiation. This strategy enables optical and remote control and/or activation of materials, substances and processes (depending on the Payload, which might comprise an enzyme, catalyst, luminescent molecule, etc.) with previously unattainable control, especially in regard to penetration depth. The multi-photon responsive elements and self-immolative oligomers may form a polymeric structure similar to a backbone, as depicted in FIG. 3, or they may be used in a dendritic structure, such as in FIG. 2. In another approach multi-photon responsive elements are directly incorporated within the polymeric backbone of materials wherein they are able to absorb two photons simultaneously to initiate a cascade of changes within a higher order assembly.

Both the backbone form and the dendritic form, or combinations thereof, may be, in turn, used as crosslinkers in a molecular network in the present invention.

Embodiments of the present invention further provide for the activation of processes within an organism brought about by the release of Payload(s) non-invasively, with a previously unattainable control of depth and location. In some embodiments of the present invention, when a single responsive molecular unit, repetitively built into the molecular network of a material, nanoparticle and/or microparticle simultaneously absorbs two photons, the changes in that molecular unit cause the molecular network of the material, nanoparticle and/or microparticle to virtually disintegrate at a precise time and location chosen by the practitioner of the invention, brought about by the destruction of the crosslinkers.

Additionally, embodiments of the present invention also provide polymers as well as materials, nanoparticles and/or microparticles that have an amplified response to multi-photon irradiation. In a non-limiting example, when a single responsive molecular unit that is repetitively embedded in a polymer, such as one used to construct a material, nanoparticle, and/or microparticle, simultaneously absorbs two photons, changes in that molecular unit cause a domino effect that unravels the entire material as a whole. The effect of a single two-photon absorption is amplified throughout the molecular network because it triggers the self-immolative property of the molecular network leading to the networks disintegration. Thus, a single event, the absorption of two-photon irradiation can produce multiple events resulting in the release of a Payload(s), and the release of the Payload(s), in turn, may also trigger multiple events.

Embodiments of the present invention may produce an amplified response to two-photon-driven processes non-invasively, even beneath bulk turbid media, such as within the tissue of a living organism. This invention enables previously unattainable optical remote control and/or activation of materials, substances and processes. Even if the two-photon irradiation is attenuated, the amplification inherent in the present invention allows functioning of present invention in spite of this attenuation.

In some embodiments of the present invention, the collective response from the Payload(s) also amplifies the desired effect, making the entire system many times more sensitive. Thus, in the art, where a practitioner may have been forced to search for a small number of single two-photon absorption events, in embodiments of the present invention, by careful selection of appropriate Payload(s), may amplify the result. Thus, when the absorption of multi-photon irradiation causing the disruption of a molecular network fabricated according to the teachings of the present invention releases a Payload(s), the Payload(s) may in turn trigger processes or events.

In a non-limiting example, a combination of nanoparticles may be used where the Payload(s) in one set may comprise a luminescent enzyme and the Payload(s) in the other set may comprise the enzyme's substrate. A small number of multi-photon absorption events may then result in a significant burst of luminescence as the enzyme and substrate are united.

In another non-limiting example, the Payload(s) can consist of antibodies. In this case, a single multi-photon absorption event can release multiple antibodies capable of binding multiple antigens at the point of release. This is in sharp contrast to the case where a single two-photon label attached to an antibody releases only a single antibody.

Yet another example is Payload(s) consisting of small molecule anticancer drugs. See, e.g., Schoell, I., G. Boltz-Nitulescu, and E. Jensen-Jarolim. 2005, "Review of novel particulate antigen delivery systems with special focus on treatment of type I allergy", *Journal of Controlled Release* 104:1-27.

According to embodiments of the present invention, materials and/or molecular networks are provided that have an amplified, and thus highly sensitive response, to non-invasive multi-photon irradiation. One approach of the instant invention is to incorporate self-immolative cross-linkers into materials that comprise the network forming nanoparticles and/or microparticles so as to amplify their sensitivity to light and allow for highly sensitive and triggered fragmentation at targeted sites. When multi-photon responsive molecular units are incorporated within a material, nanoparticle and/or microparticle in such a manner, they can initiate a cascade of changes within the material, nanoparticle and/or microparticle when triggered, disrupting the structure of the material, nanoparticle and/or microparticle. This strategy enables optical and remote control and/or activation of materials, substances and processes (depending on the Payload, e.g., an enzyme, a catalyst, an APA, etc.) with previously unattainable control, especially in regard to penetration depth, as well as a response that is amplified with respect to the multi-photon absorption event.

The instant inventive methods and compounds may be applied towards non-invasive surgery, drug delivery, diagnostic techniques, and non-invasive suture removal as well as other techniques such as injectable implants that harden upon irradiation with two photons. When self-immolative systems coupled to multi-photon responsive elements are used as crosslinkers in a nanoscale or microscale hydrogel loaded with bioactive agents, the release and activity Payload (e.g. enzymes) will be triggered by absorption of IR-light. By forming a cage around the Payload(s) that can be uncoupled remotely, the present invention provides a 'locate and release' technology enabling the effective delivery of a cargo encapsulated in nanoparticles or microparticles to specific areas.

The instant invention overcomes logistical issues that have heretofore increased the difficulties inherent with commercialization of many drug delivery systems, such as serum instability and short storage life. The instant invention provides the pharmaceutical worker in the art with methods to deliver drugs in a more accurate and more cost-effective manner as well as providing means for evaluating their performance.

The instant invention provides advantages in the diagnostics arena where it can be used to enhance the early diagnosis of disease, which, in turn, improves the possibility of successful treatment. While two-photon imaging, because of its inherent penetrating power, could be used directly to image events and conditions within tissues; the present invention enhances to capabilities of the technique. By providing a non-linear and amplified response, the present invention enhances the power of imaging using two-photon imaging. If the nanoparticle and/or microparticle of the invention is localized by affinity to an area of interest, e.g., a metastatic tumor's location, the amplified response of the present invention increases the ease of detection.

These applications open to the present invention are facilitated by the ability of the present invention to easily tune the size, chemistry, topology, and the biological response of these materials through chemical design, synthesis and engineering. Encapsulation of viral particles, DNA, proteins, and adjuvants, in the same nanoparticle may help to realize optimal cytotoxic T lymphocytes (CTLs) responses and antibody responses by sequestering the vaccine components until they reach the target cell, delivering them to a particular class of cells, and/or aiding in their presentation via the desired pathway. Moreover, with the development of new adjuvants, gene based vaccines and other multi-modal approaches to vaccination, it becomes increasingly important to use carriers tailored to these novel immunization approaches.

It should be appreciated that certain features of the present invention that are, for clarity reasons only, described in the context of separate embodiments, may also be provided as part of the present invention in combination in a single embodiment. On the other hand, various features of the invention, which are, for clarity purposes only, described in the context of a single embodiment. May also be provided separately or in any suitable subcombination.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention illustratively described herein can suitably be practiced in the absence of any element or elements, limitation or limitations that is not specifically disclosed herein. Thus, for example, the terms "comprising," "including," "containing," etc. shall be read expansively and without limitation. Furthermore, although elements of the present invention has been defined broadly with the compositions and/or methods of the invention comprising a variety of elements, in particular embodiments, individual elements may be claimed as "consisting of" or "consisting essentially of" that individual element.

Additionally, the terms and expressions employed herein have been used as terms of description and not of limitation, and there is no intention in the use of such terms and expressions of excluding any equivalent of the invention shown or portion thereof, but it is recognized that various modifications are possible within the scope of the invention claimed. Thus, it should be understood that although the present invention has been specifically disclosed by preferred embodiments and optional features, modifications and variations of the inventions embodied herein disclosed can be readily made by those skilled in the art, and that such modifications and variations are considered to be within the scope of the inventions disclosed herein. The inventions have been described broadly and generically herein. Each of the narrower species and subgeneric groupings falling within the generic disclosure also form the part of these inventions. This includes within the generic description of each of the inventions a proviso or negative limitation that will allow removing any subject matter from the genus, regardless or whether or not the material to be removed was specifically recited. In addition, where features or aspects of an invention are described in terms of the Markush group, those schooled in the art will recognize that the invention is also thereby described in terms of any individual member or subgroup of members of the Markush group. Further, when a reference to an aspect of the invention lists a range of individual members, as for a non-limiting example, 'the letters A through F, inclusive,' it is intended to be equivalent to listing every member of the list individually, that is 'A, B, C, D, E and/or F,' and additionally it should be understood that every individual member may be excluded or included in the claim individually. Additionally, when a reference to an aspect of the invention lists a range of individual numbers, as for a non-limiting example. '0.25% to 0.35%, inclusive,' it is intended to be equivalent to listing every number in the range individually, and additionally it should be understood that any given number within the range may be included in the claim individually.

The steps depicted and/or used in methods herein may be performed in a different order than as depicted and/or stated. The steps are merely exemplary of the order these steps may occur. The steps may occur in any order that is desired such that it still performs the goals of the claimed invention.

Furthermore, although the present invention has been described in conjunction with specific embodiments thereof, it is evident that many modifications, alternatives, and variations will be apparent to those skilled in the art. Accordingly, the present invention should be construed to embrace all such modifications, alternatives, and variations that fall within the spirit and broad scope of the claims.

All publications, patents, and patent applications mentioned in this specification are hereby incorporated in their entirety by reference into the specification to the same extent as if each individual publication, patent, or patent application was specifically and individually indicated to be incorporated herein by reference. In addition, citation or identification of any reference in this application shall not be construed as an admission that such reference is available as prior art to the present invention.

Definitions

As used herein, the term "Payload", or "Payload(s)", refers to any compound of interest that can be incorporated into the molecular network of the present invention. Non-limiting examples of Payloads comprise chemicals such as drugs, APAs, pharmaceutical agents, and/or radioactive elements; a Payload can also comprise proteins such as antibodies, antibody fragments, antigens, cytokines; a Payload can also comprise nucleic acids, including DNAs, RNAs, siRNAs, antisense oligonucleotides; a Payload can also comprise detectable labels, such as fluorescent compounds (e.g., rhodamine dyes, near infrared fluorescent agents, or fluorescent proteins) and MRI contrast agents; and/or a Payload can also comprise a cocktail that comprises more than one compound (e.g., a pharmaceutical agent and an antibody). In the embodiment where a Payload consists of multiple entities, each may be present separately within the nanoparticle and/or microparticle or some of the entities may be conjugated together in various combinations. Furthermore the multiple entities may be present in separate particles and the particle may be combined for use. The Payload(s) delivered by the embodiments of the present invention may routinely contain pharmaceutically acceptable concentrations of salts, buffering agents, preservatives, compatible carriers, and optionally other therapeutic agents. In preferred embodiments of the present invention the Payload(s) is not covalently attached to the molecular network of the invention.

As used herein the terms "multi-photon responsive element" and "multi-photon responsive moiety" have equivalent meanings.

As used herein, the term "tier" refers to the a generation, or a level, in a dendritic structure.

As used herein, the term "amplifying sensitivity", or "amplifying", refers to where the number of Payload molecules released is greater than the number of covalent bonds cleaved during the release step. The term "amplifying" may also refer to the where the absorption of multi-photon irradiation that results in the cleavage of a multi-photon responsive element, causes in turn the cleavage of self-immolative oligomers covalently attached to the multi-photon responsive element. The term "amplifying sensitivity" also refers to, in the area of detection, where the signal resulting from two-photon irradiation is substantially stronger than can be accounted for by the irradiation itself As used herein, the term "particle" refers to small particles assembled according to embodiments of the present invention. The term "particle" may refer to nanoparticles or microparticles or both.

The term "microparticle", as used herein, generally refers to a particle between 0.1 and 200 micrometers in size.

The term "nanoparticle", as used herein, generally refers to discrete structures that are at least under 200 nm in diameter, in other words, significantly less than the diameter of a capillary. (See, e.g., Singh, R., J. W. Lillard Jr., Exper Mol Path 86 (2009) 215-223.) The term "nanoparticle" may also refer to particles that are between 1 nm and 100 nm in diameter. Some of the novel properties associated with nanoparticles, which differentiate them from bulk materials, is generally associated with their size being less than 100 nm.

Microparticles and/or nanoparticles can be formed by a wide variety of means and with widely varying compositions. Examples include hydrogels such as acrylamide micelle polymerization. The may also be created from such diverse substances as poly(D,L) lactides; poly (lactic acid) ("PLA"); poly (D,L glycolide) ("PLG"); poly(lactide-co-glycolide) ("PLGA"); and poly-cyanoacrylate ("PCA") (Singh, R., J. W. Lillard Jr., Exper Mol Path 86 (2009) 215-223). Microparticles and/or nanoparticles can also be created from various forms of micelles/liposomes; such micelles/liposomes can be assembled via emulsions or through a process of depositions. Acrylamide hydrogels, such as ones made from N-isopropylacrylamide (NIPAAm) and acrylamide (AAm) have been made incorporating gold-gold sulfide nanoshells designed to strongly absorb near-infrared light, e.g., wavelengths between 800 and 1200 nm. When these nanoparticles are irradiated, the temperature is increased, causing in turn the release of associated molecular cargo (Sershen S R, Westcott S L, Halas N J, West J L; Temperature-sensitive polymer-nanoshell composites for photothermally modulated drug delivery; J Biomed Mater Res. (2000) 51(3):293-98. Examples of microparticles and/or nanoparticles also include dendrimers (see, e.g., Cheng, Y., J. Wang, T. Rao, X. He, T. Xu, T.; *Pharmaceutical applications of dendrimers: promising nanocarriers for drug delivery*; Front. Biosci. 13 (2008) 1447-1471). Types of microparticles and/or nanoparticles have also been described in PCT US2007/006844.

Microparticles and/or nanoparticles can also be formed according to the teachings of the present invention.

The term "molecular network", or the term "molecular cage", as used herein refers to a covalently bound network comprising polymers that comprise polyacrylamide, or its equivalent, and further may comprise PEG, or its equivalent, and where these polymer(s), together with PEG or its equivalent, are covalently attached to self-immolative oligomer(s) which are covalently attached to multi-photon responsive element(s).

The terms "administration" or "administering" refer to a method of incorporating a compound into the cells or tissues of an animal, preferably a mammal, in order to treat or prevent an abnormal condition. When the composition of the invention is provided in combination with one or active agents, the terms "administration" or "administering" include sequential or concurrent introduction of the composition with the other agent(s). For cells harbored within the organism, many techniques exist in the art to administer compounds, including (but not limited to) oral, injection, parenteral, dermal, and aerosol applications.

EXAMPLE 1

Microparticles have previously been developed where one triggering event leads to the cleavage of one bond (signal-to-output ratio equals 1). (See, e.g., Cohen, Almutairi et al., supra] In some embodiments of the instant invention, however, a single triggering event leads to the number of cleaved bonds equal to the number of branches (in the case of dendritic crosslinker), or to the number of monomer units (in the case of linear polymeric crosslinkers), thus providing a greatly amplified response. To demonstrate the feasibility of this approach a first generation dendritic crosslinker is compared with a second generation dendritic crosslinker in Example 1.

Figure 7:
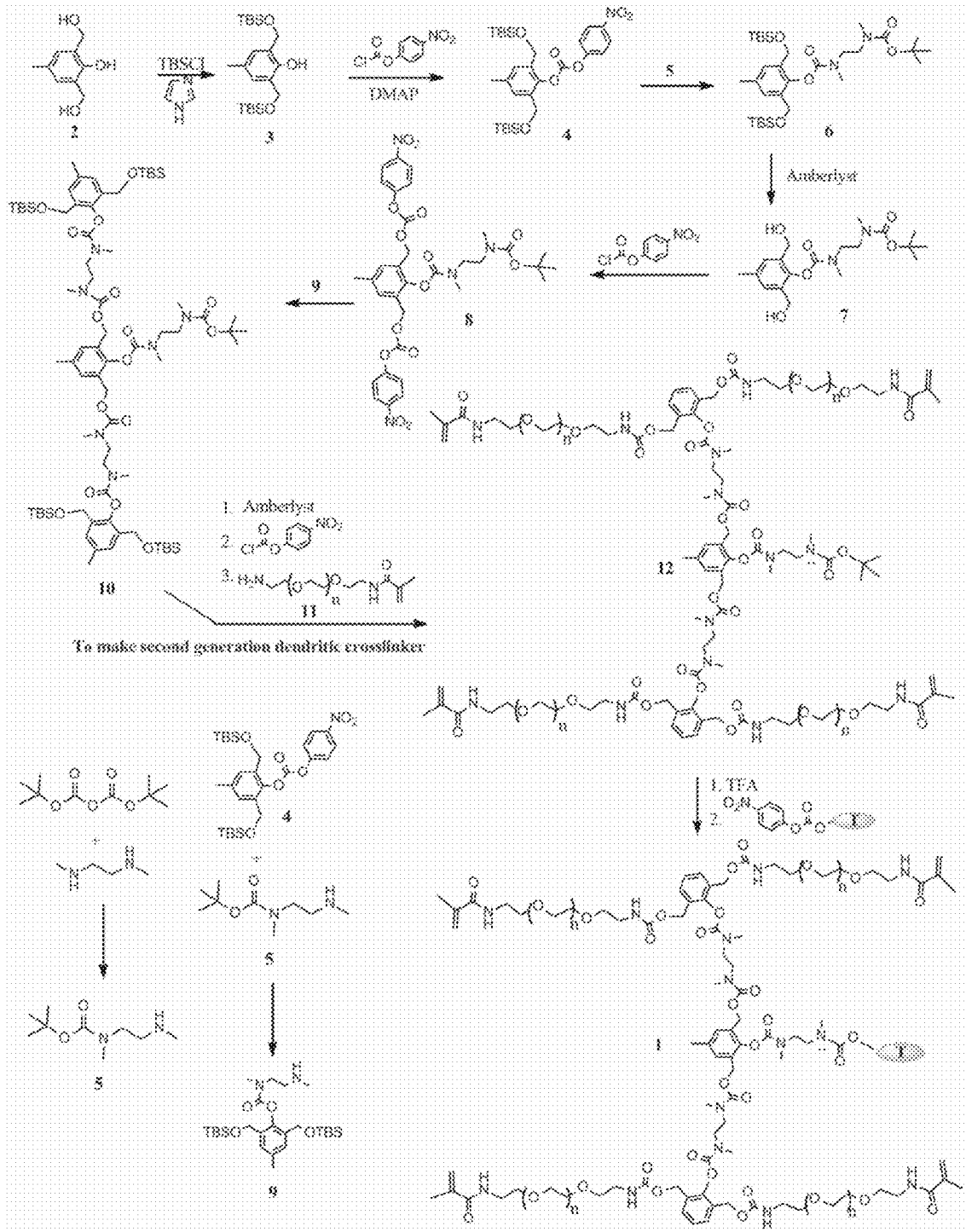
FIG. 7 is a diagram representing synthesis of dendritic self-immolative crosslinker 1, in which compound 8 is reacted with compound 11 to form the first generation dendritic crosslinker. Compound 11 is synthesized in one step from mono-protected PEG diamine with methyl acrloyl chloride.

The synthesis of crosslinker 1 is outlined in FIG. 7. Compound 4 can be synthesized from commercially available 2,6-bishydroxymethyl-p-cresol, 2, by first protecting the benzylic alcohol groups of 2 with tert-butylsilylchloride (TBSCI) to give compound 3, and then reacting it with p-nitrophenyl-chloroformate in the presence of catalytic amount of 4-dimethylaminopyridine (DMAP). Compound 5 can be obtained from commercially available N,N'-dimethyl-ethylenediamine and di-t-butyl dicarbonate (Boc anhydride).

Reacting compound 4 with compound 5 produces compound 6. Removal of the protecting groups with Amberlyst™ followed by reaction with p-nitrophenyl-chlorophormate yields compound 8. Compound 9 can be obtained by reaction of 4 with 5 followed by removal of the Boc protecting group. Reacting compounds 8 and 9 yields compound 10. Deprotection of the hydroxyl groups of compound 10 followed by conversion into p-nitrophenyl-carbonates and reaction with compound 11 yields compound 12. A triggering group can be attached by reacting compound 12 with the corresponding p-nitrophenylcarbonate to furnish the desired self-immolative dendritic cross-linker 1.

Bromo-coumarin 13, a well established class of two-photon protecting groups, was used as a two-photon photoremovable protecting group.

EXAMPLE 2

Monomer 1 was synthesized largely according to a previously published procedure (Amir, R. J.; Pessah, N.; Shamis, M.; Shabat, D. Angew. Chem., Int. Ed. 2003, 42, 4494-4499) with slight modifications. 4,5-Dimethoxy-2-nitrobenzyl alcohol (Patchornik, A; Amit, B.; Woodward, R. B. J. Am. Chem. Soc. 1970, 92, 6333-6335) was chosen despite its low two-photon uncaging cross-section (0.01 GM) (Aujard, I, Benbrahim, C, Gouget, M, Ruel, O, Baudin, J. B., Neveu, P, *Chem. Eur. J.* 2006, 12, 6865-6879) compared to 4-bromo-coumarins (1 GM) (Furuta, T., Wang, S. S. H., Dantzker, J. L., Dore, T. M., Bybee, W. J., Callaway, E. M., Denk, W. Tsien, R. Y., *Proc. Natl. Acad. Sci. U.S.A.,* 1999, 96, 1193-1200) or fluorene-based systems (5 GM) (Gug, S, Bolze, F. Specht, A. Bourgogne, C. Goeldner, M. Nicour, J.-F., Angew. *Chem. Int. Ed.,* 2008, 47, 9525-9529), because it is well-studied and readily available, making it a good proof-of-concept photolabile group.

Monomer 1 was copolymerized with adipoyl chloride to yield a regular copolymer. The low molecular weight oligomers were removed by repeated precipitation of the crude polymer with cold ethanol, yielding the final product with a molecular weight of 65,000 Da and PDI of 1.54 (characterized by GPC relative to polystyrene standards) with 44% yield.

Cleavage of the multi-photon responsive element triggering groups by irradiation at 350 nm and 750 nm, via one and two-photon processes respectively, was monitored by observing the changes in the absorbance spectrum of polymer 2 in acetonitrile/$H_2O$(9/1). Upon light exposure, the peak at 346 nm, corresponding to 4,5-dimethoxy-2-nitrobenzyl carbamate decreased, while a new peak at 400 nm appeared, corresponding to the cleaved 4,5-dimethoxy-2-nitrosobenzaldehyde. The absorption spectrum remained unchanged after 15 minutes of irradiation with 350 nm light, indicating complete deprotection, while it was necessary to irradiate the system for 5 hours at 750 nm to observe changes in the absorption spectrum, consistent with the low two-photon uncaging cross-section of 4,5-dimethoxy-2-nitrobenzyl group.

Figure 13:
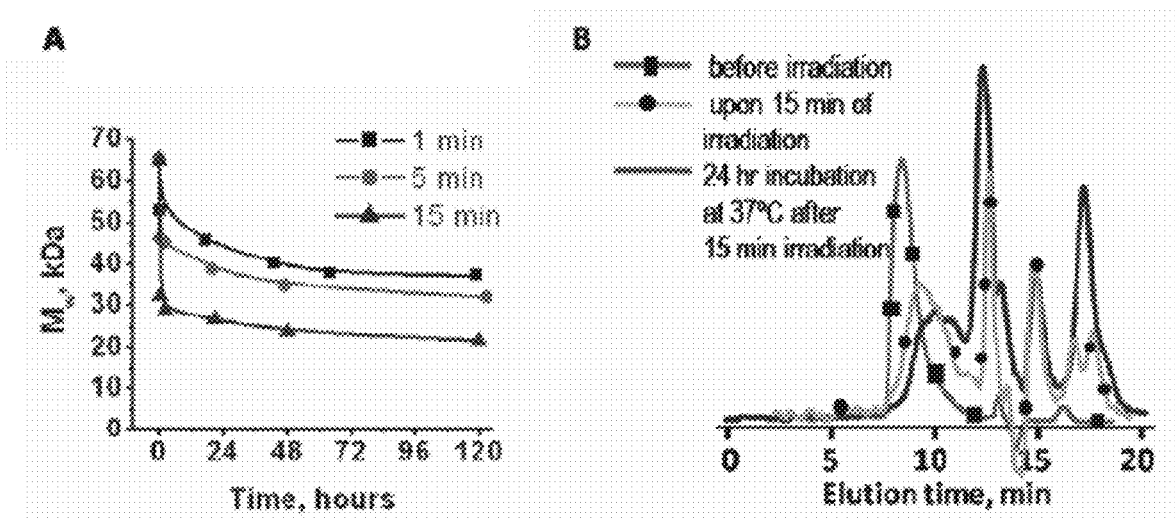
FIG. 13 depicts (A) the degradation of polymer upon exposure to 350 nm light for defined time periods in acetonitrile/H2O (9/1) and (B) GPC traces of polymer 2 before irradiation (boxes), upon irradiation for 15 min in acetonitrile/H20/Et3N (9/0.5/0.5) (circles) and after 24 hr incubation at 37° C. after 15 min irradiation.

The degradation of polymer 2 was studied by GPC and proton NMR in acetonitrile/water solutions. The polymer solutions were exposed to UV light (350 nm) for various periods of time and incubated at 37° C. Samples were removed and analyzed. The degree of polymer degradation showed strong dependence on the irradiation time (FIG. 13). The initial drop in molecular weight in the first few minutes after UV irradiation is likely to be mostly due to the loss of the triggering groups, while further reduction in molecular weight is due to the cleavage of the polymer backbone as a result of cyclization and elimination reactions within the self-immolative monomer unit. The difference in the degradation degree is especially evident in the samples irradiated for 5 and 15 minutes: more multi-photon responsive element triggering groups are cleaved. Consequently, the polymer chains degrade into smaller fragments. Although the estimated molecular weights of the fragments level off at 20,000 Da the molecular weight of monomer 1 (m/z=544.19) was estimated by GPC to be 3,500 Da, therefore these fragments may be oligomers. Notably, only a small portion of all the multi-photon responsive element triggering groups need to be cleaved to induce a reduction in the molecular weight of the polymer.

The proton NMR of polymer 2 before irradiation in $CDCl_3$ showed all the characteristic peaks and splittings. As expected, in $CD_3CN/D_2O$ the NMR peaks broadened. Upon irradiation and incubation at 37° C. for 18 hours the NMR peaks corresponding to the benzylic protons of 4,5-dimethoxy-2-nitrobenzyl group disappeared and the remaining peaks shifted accordingly. Sharper monomer peaks, indicating the presence of urea and cresol emerged, overlapping with broader polymer and oligomer peaks.

Figure 14:
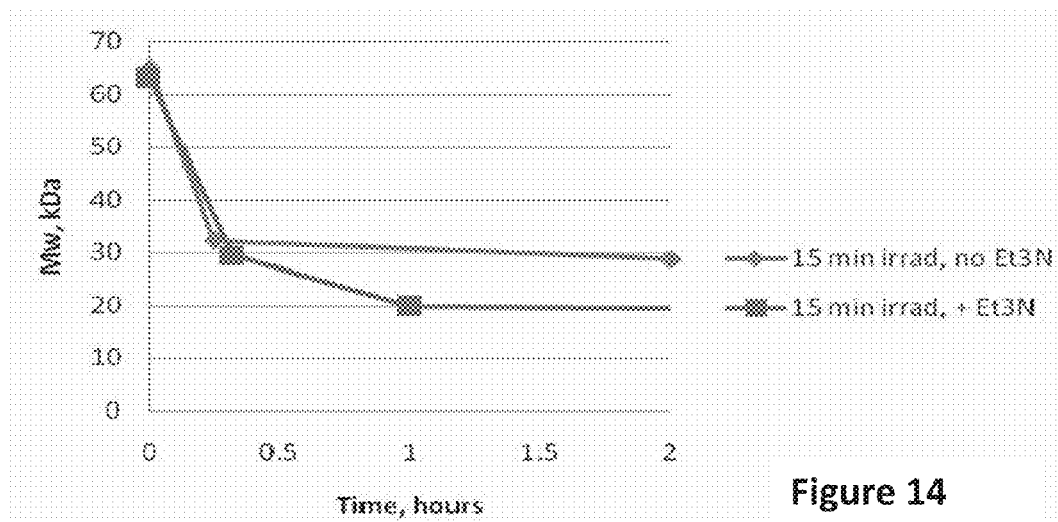
FIG. 14 depicts the degradation of polymer 2 in $CH_3CN/H_2O(9/1)$ (circles) and in $CH_3CN/H_2O/Et_3N$ (9/0.5/0.5) (boxes) after 15 min of UV irradiation followed by incubation at 37° C.
Figure 15:
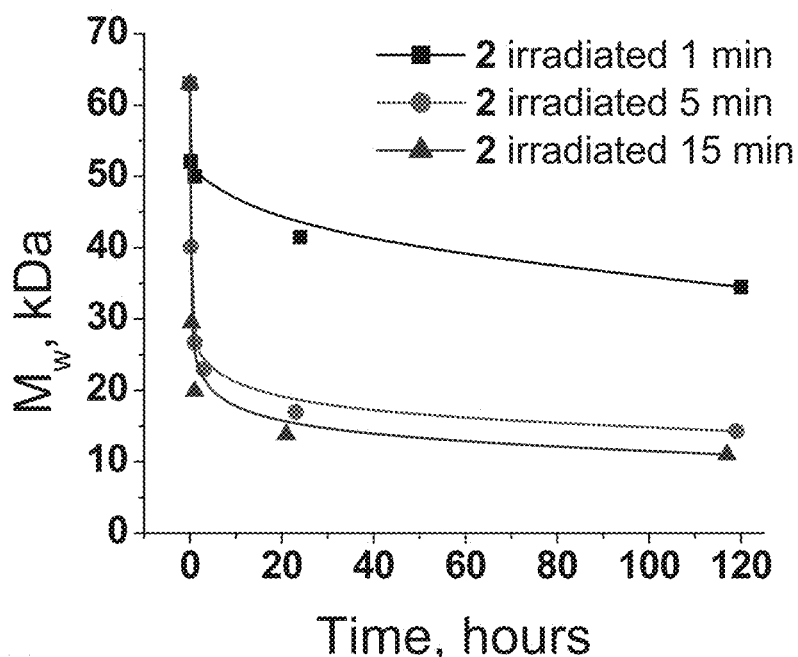
FIG. 15 depicts the degradation of polymer upon exposure to 350 nm light for defined time periods in acetonitrile/$H_2O/Et_3N$ (9/0.5/0.5). The boxes represent 1 min of irradiation, circles 5 min, triangles 15 min.

The cyclization of the diamine linker has been shown to be the rate-determining step of the self-immolation within the quinine-methide unit, and it has been shown to accelerate in the presence of triethylamine (Amir, R. J.; Pessah, N.; Shamis, M.; Shabat, D.; *Angew. Chem., Int. Ed.* (2003) 42, 4494-99). Thus, we measured polymer degradation in the presence of triethylamine (FIG. 15) and observed an increase in the rate of the polymer degradation (FIG. 14).

Figure 16:
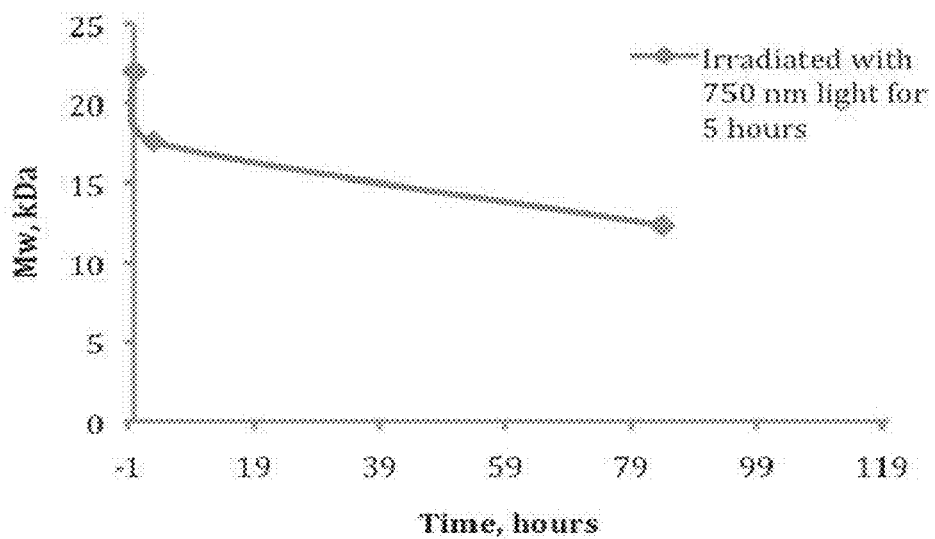
FIG. 16 depicts the degradation of polymer upon exposure to 750 nm light for 5 hours in acetonitrile/$H_2O$ (9/1) and incubation at 37'C.

Two-photon irradiation of polymer 2 for 5 hours showed a similar degree of degradation as 5 minute one-photon irradiation (FIG. 16).

EXAMPLE 3

To evaluate the properties of the new polymer for controlled light-triggered release, nanoparticles were formulated by the single emulsion method (FIG. 17), encapsulating the small hydrophobic molecule dye Nile Red. This small molecule was chosen because of its excellent photostability. The Z-average diameter of the nanoparticles was 170 nm and PDI=0.191, as determined by dynamic light scattering (DLS).

Figure 17:
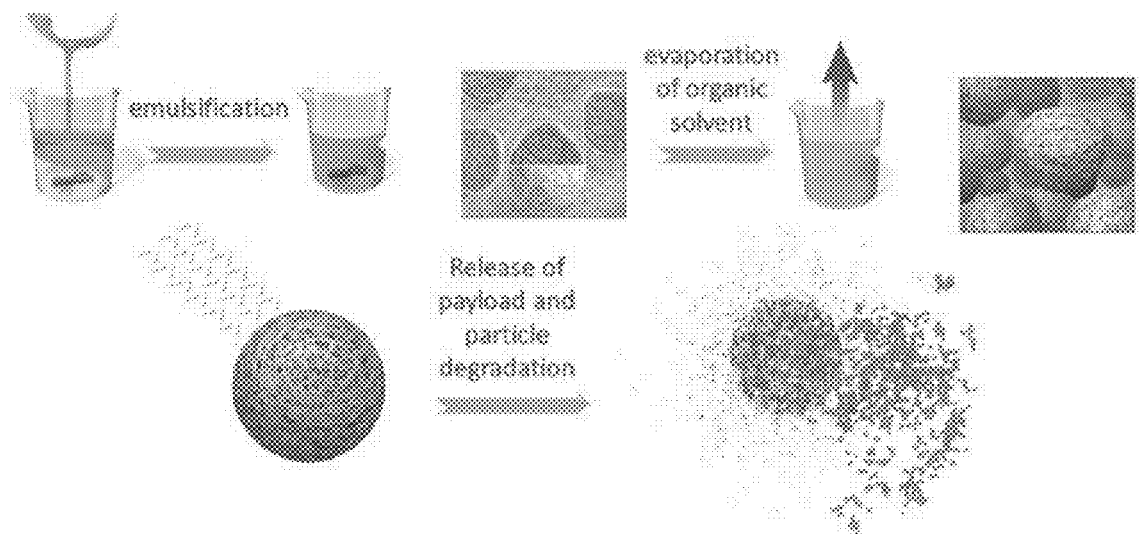
FIG. 17 is an illustration of the formulation of nanoparticles, their degradation and light-triggered release of their encapsulated Nile Red payload.
Figure 18:
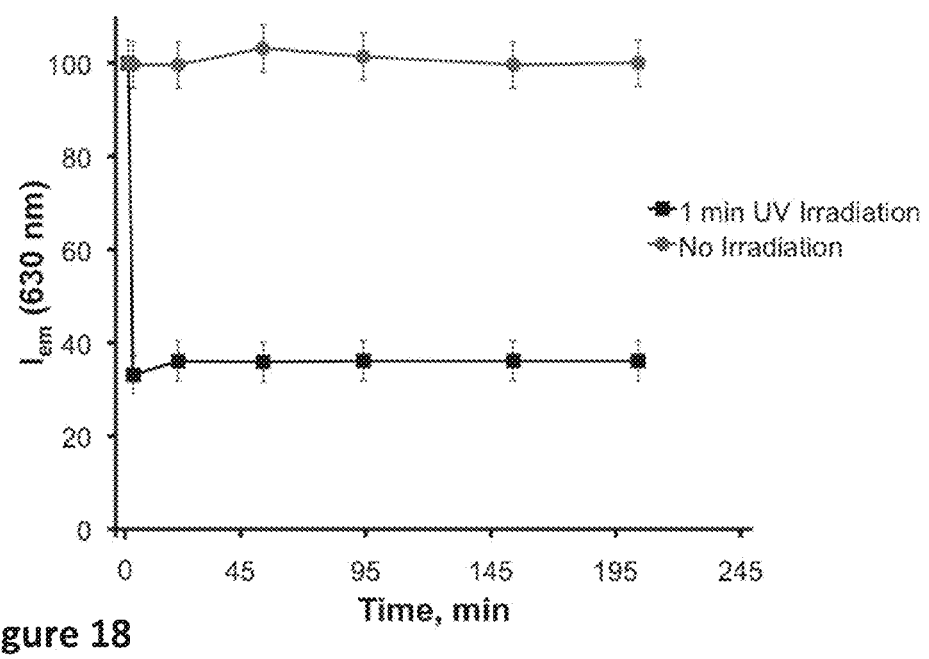
FIG. 18 depicts the fluorescence intensity of Nile Red encapsulated within polymeric nanoparticles and upon irradiation with 350 nm light, monitored at 630 nm with excitation at 540 nm.

The release of the Nile Red Payload upon irradiation was observed by fluorescence spectroscopy. Nanoparticles were redispersed in PBS pH 7.4 and the fluorescence intensity of the suspension was recorded. After irradiation with 350 nm light for 1 min, the fluorescence intensity dropped by 67%, indicating burst release of the dye from the nanoparticles into a more polar medium (FIGS. 17 and 18). On the other hand, a suspension of nanoparticles that was not irradiated exhibited unchanged fluorescence intensity over several days. Interestingly, prolonged irradiation of nanoparticles did not result in a further drop of fluorescence signal.

Figure 19:
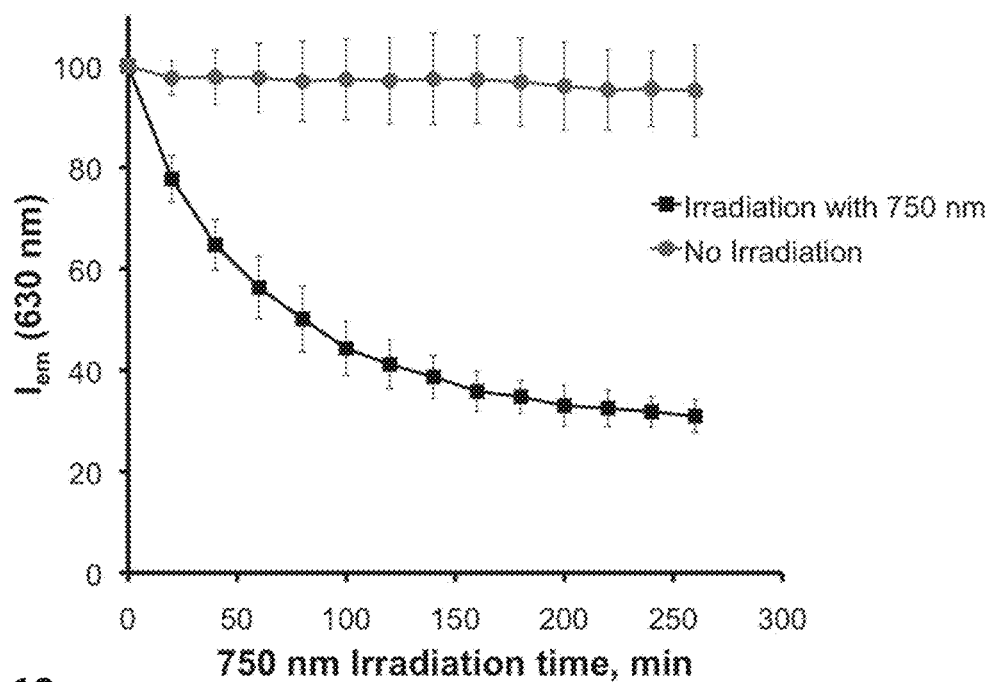
FIG. 19 depicts the fluorescence intensity of Nile Red encapsulated within polymeric nanoparticles and after 20 min irradiation increments with 750 nm light, monitored at 630 nm with excitation at 540 nm.

Further degradation of nanoparticles of 2 after UV irradiation was observed by DLS at 37° C. in PBS buffer at pH 7.4 and pH 10. No particles were detected after 4 days of incubation at pH 10 while in pH 7.4 the particles degraded within 10 days. We also explored the possibility of triggering the release of Nile Red by NIR light through two-photon absorption. The suspension of nanoparticles in PBS pH 7.4 was irradiated at 750 nm for 20 min intervals followed by 10 min of incubation at 37° C. A gradual decrease in the fluorescence intensity of Nile Red was observed during the 4 hours of irradiation (FIG. 19).

The observation of burst release of Nile Red upon UV irradiation while the polymer degradation is slower suggests the possibility of a secondary mechanism of release. A change in hydrophobicity of the particles upon cleavage of the multi-photon responsive element triggering group may be involved. The rapid and efficient unmasking of a large number of the secondary amino groups may make the particles rapidly more permeable to water. This may explain the rapid release of Nile Red upon UV irradiation. However, the two-photon unmasking process is much less efficient which could explain the slower Nile Red release in the NIR two-photon regime. Notably, the final degradation of the nanoparticles is an important property for in vivo biological applications that require materials to degrade into easily excretable fragments.

To rule out the possibility of spontaneous release caused by simple cavitation, poly(lactic-co-glycolic acid) (PLGA) nanoparticles encapsulating Nile Red were formulated by the same method and exposed to UV and NIR light in the same fashion. As expected, no release of Nile Red was observed in this case.

EXAMPLE 4

More efficient two-photon uncaging coumarin-based groups are used in place of the nitrobenzyl of Example 2, supra, group to make the system more sensitive to NIR light increase their utility. When irradiated with near infrared radiation, the nanoparticles release their payload.

EXAMPLE 5

Figure 20:
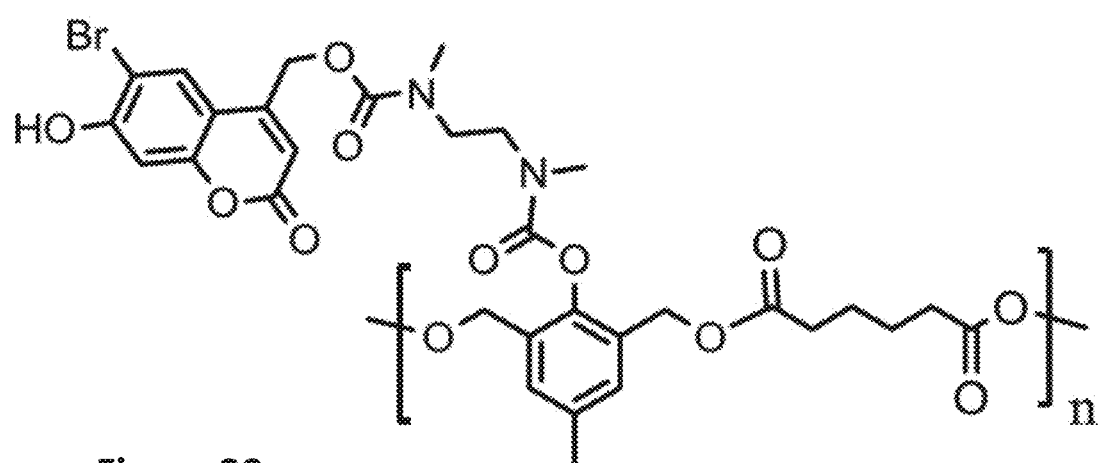
FIG. 20 represents a polymer synthesized with a 4-bromo-coumarin (1 GM) multi-photon responsive element having increased efficiency.

The versatile design of the present invention allows the multi-photon responsive element triggering group to be sensitive to internal or remote stimuli. A polymer was synthesized with a multi-photon responsive element having increased efficiency, specifically 4-bromo-coumarin (1 GM) shown in FIG. 20. Polymers made with this multi-photon responsive element degraded rapidly upon exposure to 800 nm light. Nanoparticles made from this polymer are being formulated and characterized.

EXAMPLE 6

Figure 21:
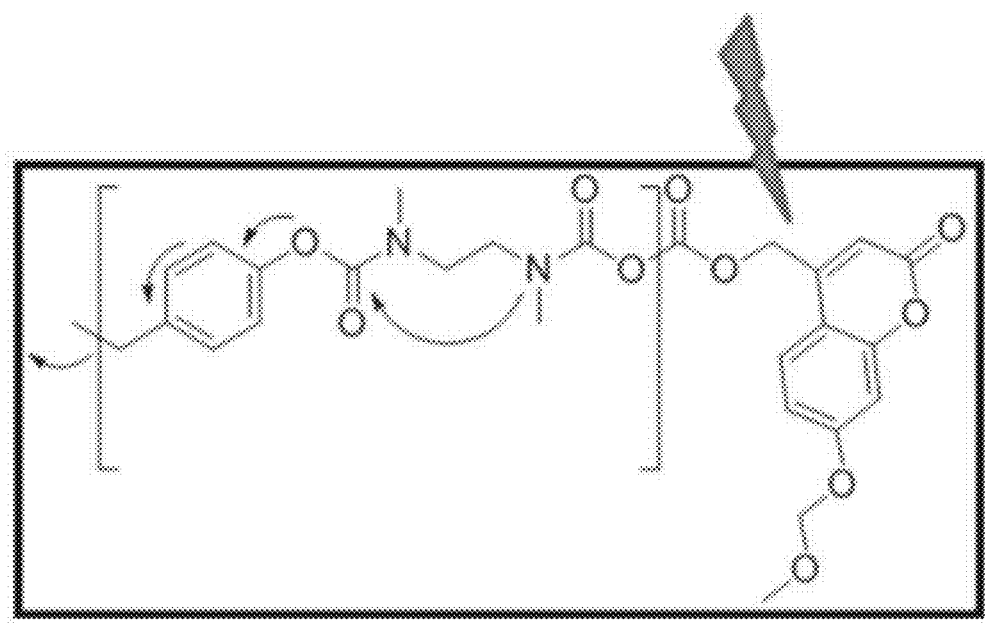
FIG. 21 represents the structure of a self-immolative polymer.
Figure 22:
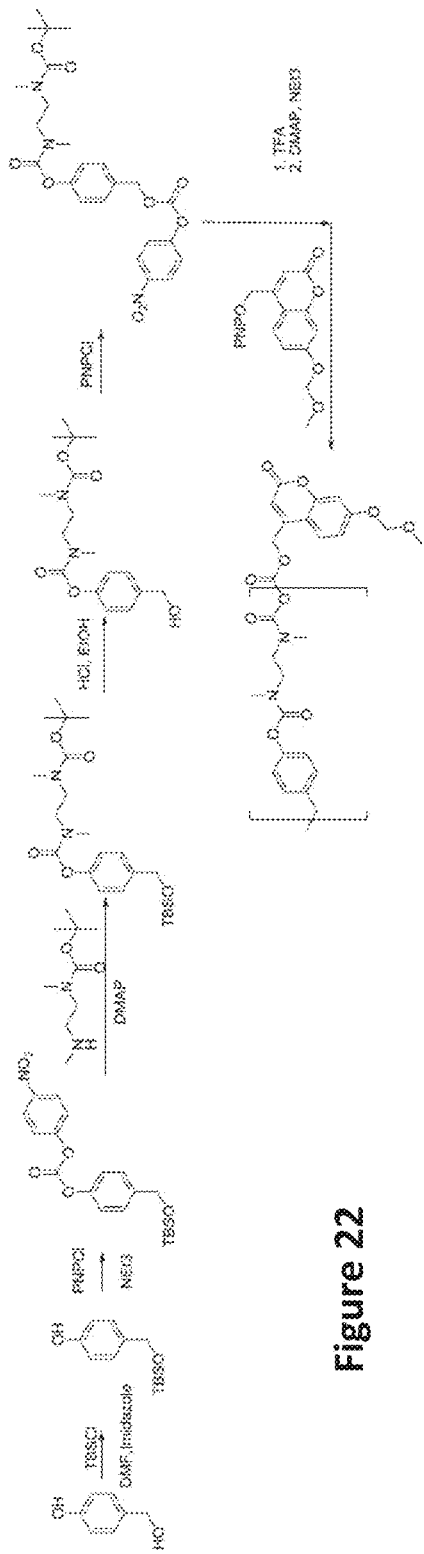
FIG. 22 represents the steps involved in the synthesis of self-immolative polymers bearing bromo-coumarin groups. This photo protecting group is cleaved efficiently upon two photon irradiation with 800 nm of light.

The self-immolative polymer shown in FIG. 21 was synthesized as shown in FIG. 22 and formulated into nanoparticles.

Its degradation properties are being characterized; the rate-determining step in the mechanism of this type of polymer degradation is the cyclization to form the cyclic urea.

EXAMPLE 7

Figure 23:
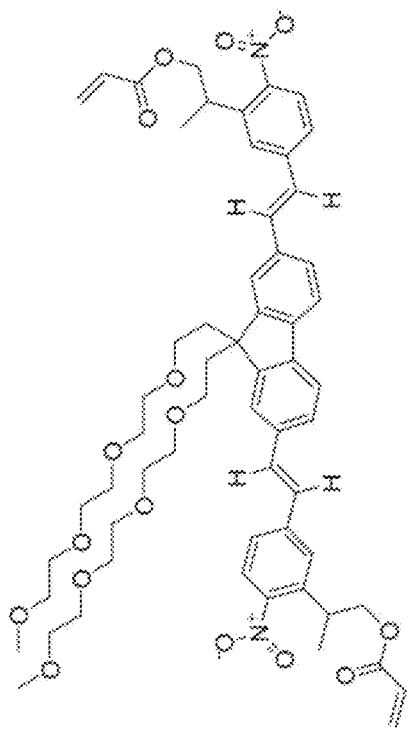
FIG. 23 represents the structure of a two-photon responsive element.
Figure 24:
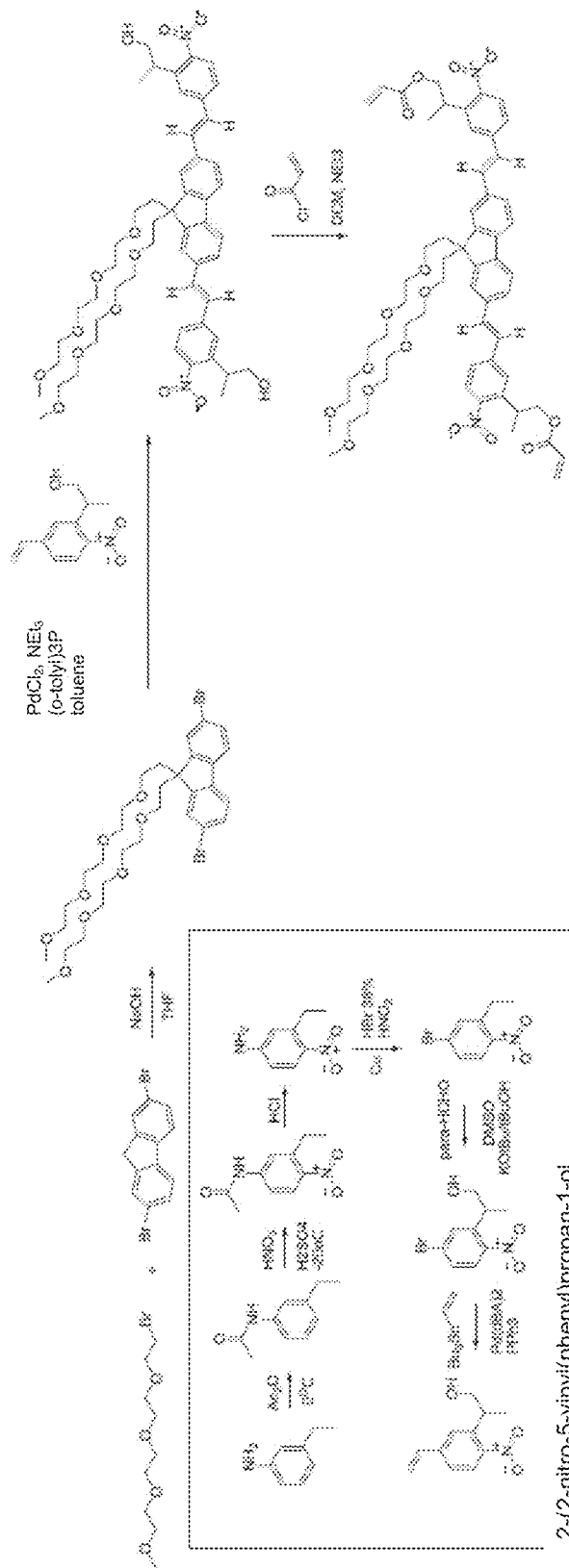
FIG. 24 represents the methods and steps used to synthesize a crosslinker comprising a multi-photon responsive element.
Figure 25A:
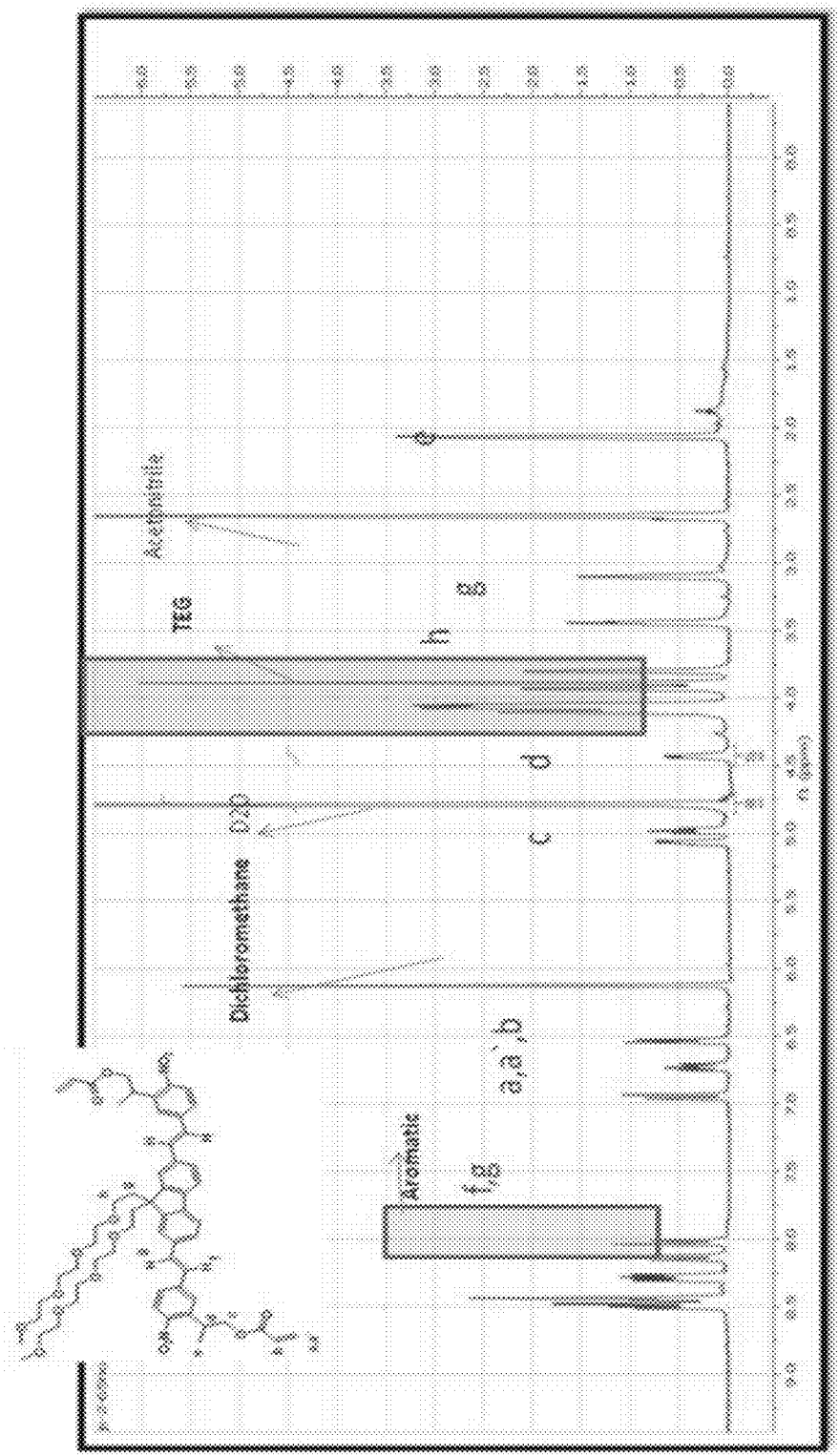
FIGS. 25a-25c represent data demonstrating the cleavage of a two-photon responsive element in response to irradiation at 800 nm.
Figure 25B:
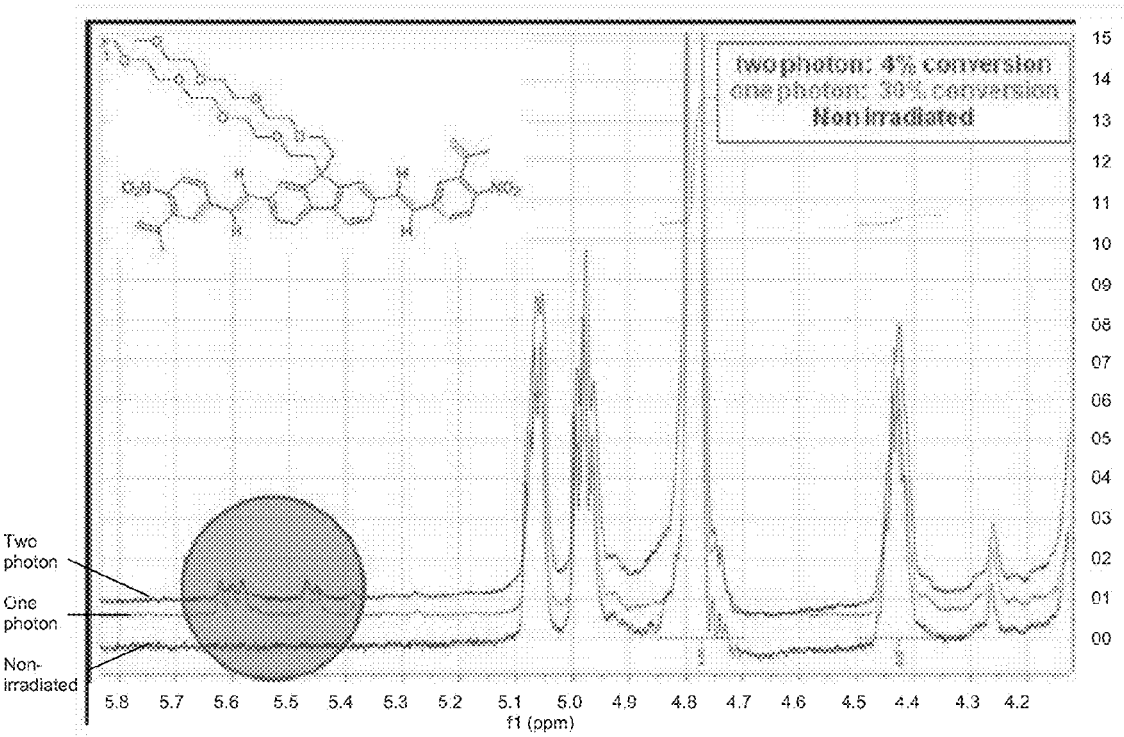
Figure 25C:
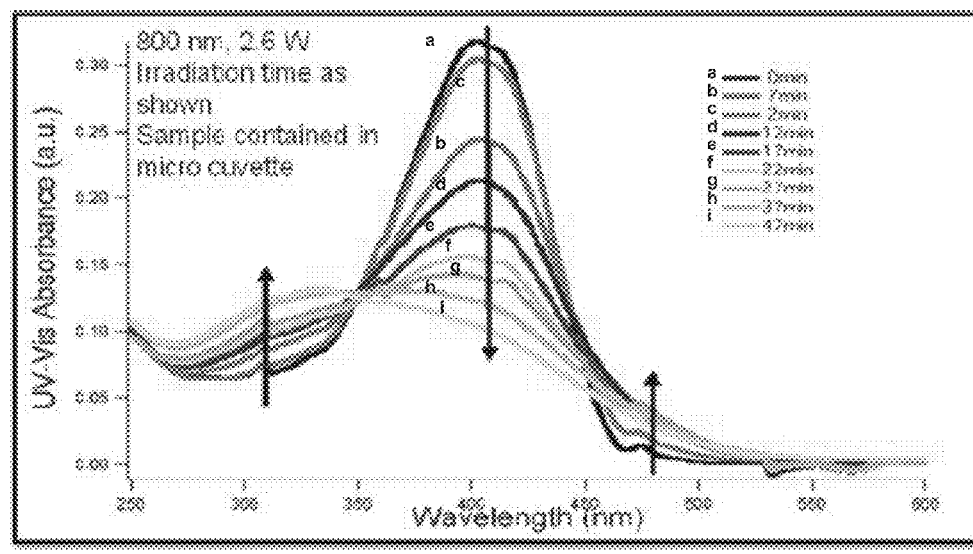

Additional two-photon-labile crosslinkers such as the one in shown in FIG. 23 were developed. This crosslinker was used to form nanoparticles and gels. The method used to synthesize this crosslinker is shown in FIG. 24. Degradation of this crosslinker was demonstrated with near-UV light as well as 800 nm light. Its cleavage was demonstrated by the results depicted in FIG. 25.

Figure 26:
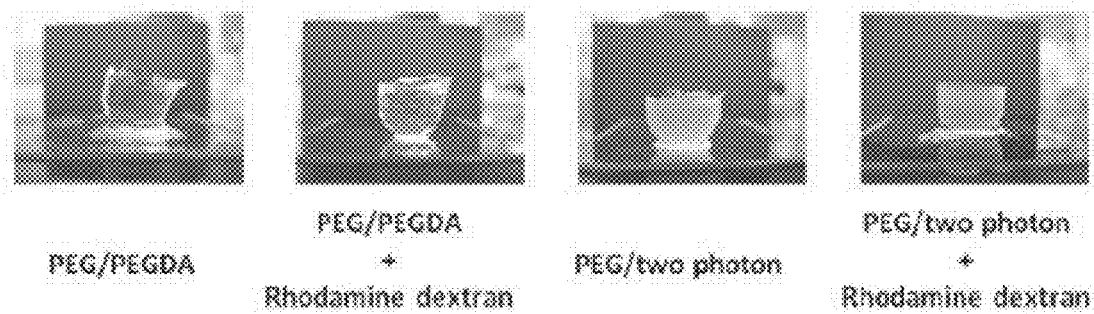
FIG. 26 reproduces photographs of hydrogels formulated by the crosslinkers containing multi-photon responsive elements.

These new crosslinkers were used to formulate two-photon-labile crosslinked hydrogels using PEG-Acrylate initiated with TMEDA, which are shown in FIG. 26. These hydrogels incorporating multi-photon responsive elements were formulated by using 480 mg of PEG-Acrylate plus 1 mol % of (PEG-Diacrylate/multi-photon) crosslinker plus 200 µl of buffer (±Rhodamine dextran) plus 20 µl of 50% APS. Formation of the gel was initiated using 20 µl of TMEDA and continued at 37° C. for 24 hrs.

Figure 27A:
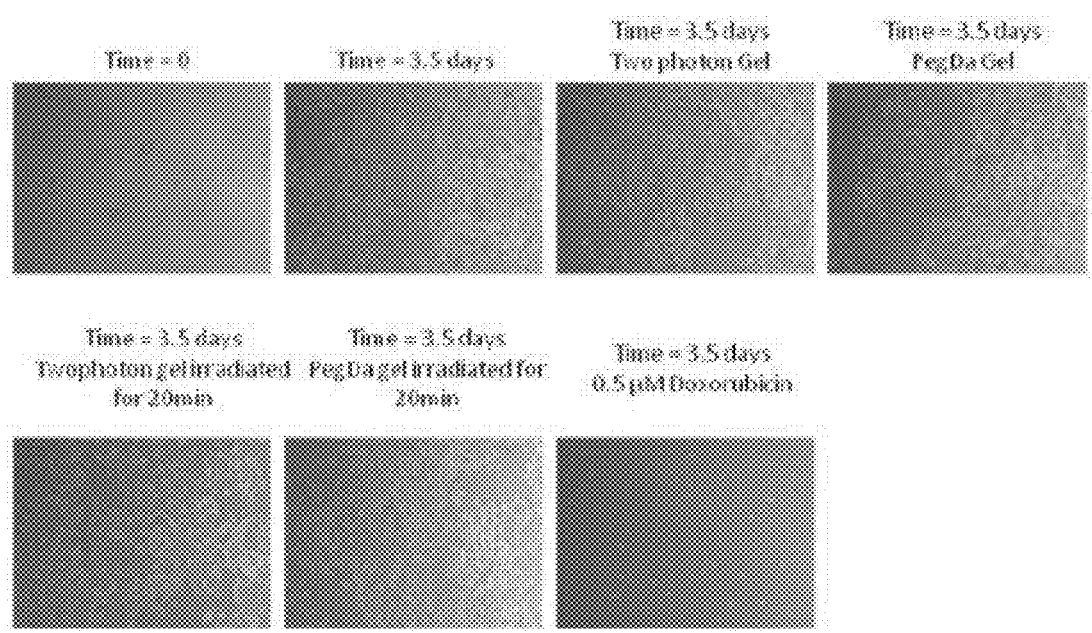
FIGS. 27a and 27b depict the results of assays showing the low toxicity of hydrogels formulated by the crosslinkers with multi-photon responsive elements. The results depicted in FIG. 27a indicate that a hydrogel synthesized with a multi-photon-responsive unit of the instant invention is not toxic when the amount of cell growth in 3.5 days with no treatment is compared with the presence of the hydrogel with the multi-photon responsive element with and without irradiation, and a PEG-Acrylate hydrogel without a multi-photon responsive element (with and without radiation). All of these treatments showed growth when compared with the negative control. The gel also showed little or no toxicity using the MTT-toxicity assay (comparing media alone, media plus irradiation, hydrogel, and hydrogel treated with irradiation.
Figure 27B:
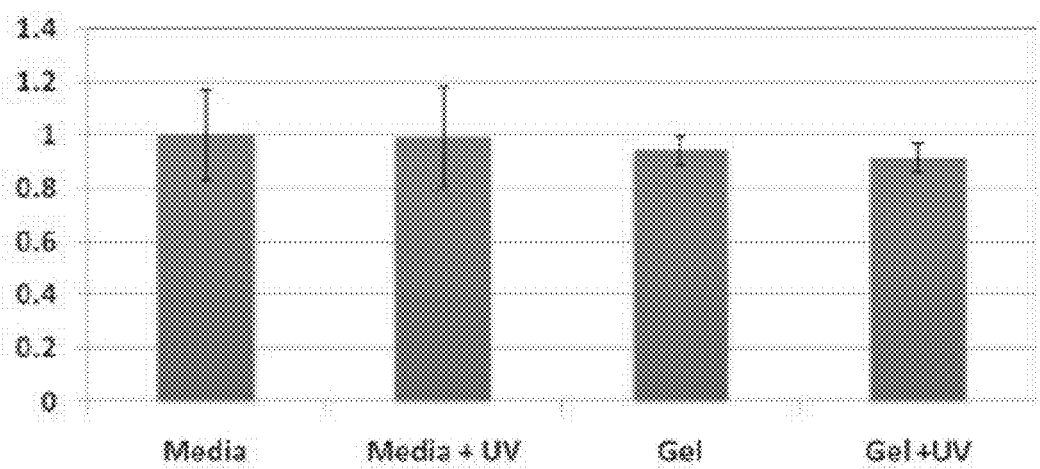

These hydrogels were demonstrated to have a low toxicity using two different assays. The results of these assays are shown in FIG. 27. Growth of cells was tested in the presence of ~30 mg of the hydrogels formulated with multi-photon-responsive elements in 2 ml of media (6-well dishes). The pieces of gel were treated or untreated with exposure to 20 minutes of UV. The multi-photon-labile gel material was also tested in the MTT-toxicity assay.

EXAMPLE 8

Figure 28:
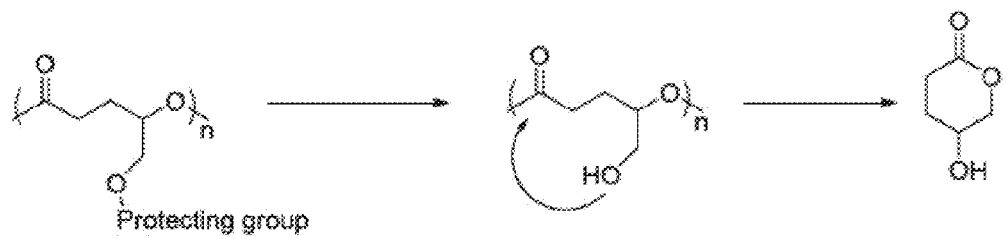
FIG. 28 depicts a polyester backbone that will disassemble upon deprotection of its hydroxyl protecting group.

Materials with polymeric backbones are synthesized wherein the backbones have been molecularly engineered to incorporate units capable of absorbing multi-photon radiation simultaneously and initiating a cascade of changes within the higher order assembly. FIG. 28 depicts one such polymer based on a polyester backbone that will disassemble upon deprotection of the hydroxyl protecting group. This polymer will undergo backbiting upon deprotection of the pendant alcohol. The alcohols are protected with a variety of protecting groups. In the initial experiments, model protecting groups such as those used elsewhere are used. Other protecting groups may be used.

Figure 29:
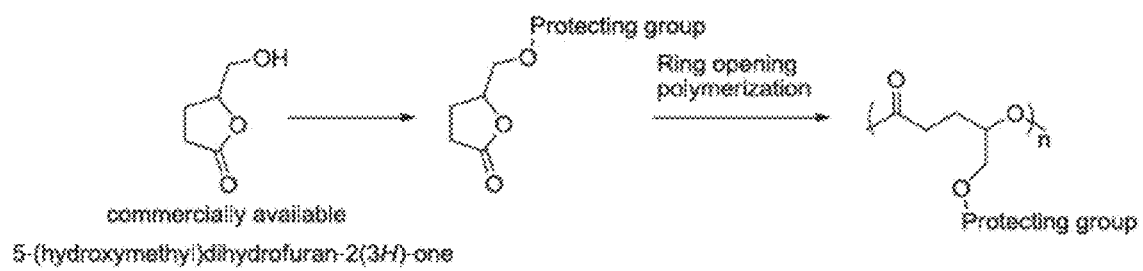
FIG. 29 depicts the method that is used to produce the self-immolative polyester backbone.

The proposed synthesis of the proposed polyester backbone is shown in FIG. 29. These polyesters will be synthesized from the commercially available butyrolactone 4-(hydroxymethyl)-1,3-dioxolan-2-one via a ring-opening polymerization using distannoxane catalysts.

This backbone may be used with the methods and compounds of the present invention.

EXAMPLE 9

Figure 30:
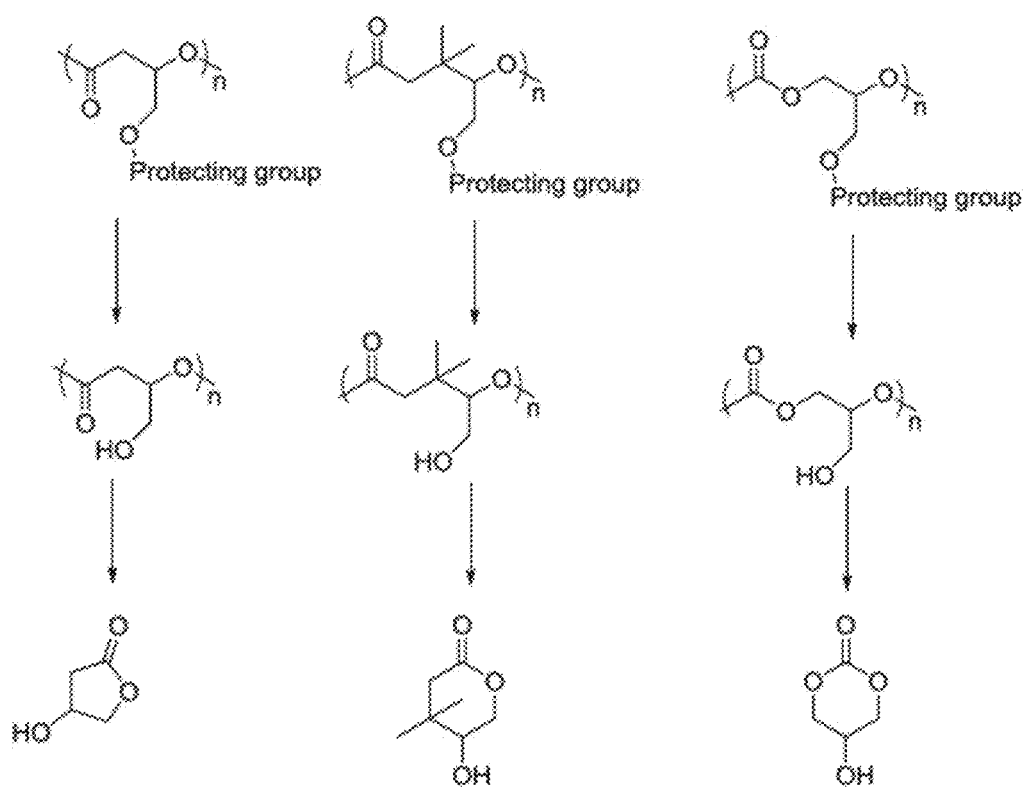
FIG. 30 depicts several polyester and polycarbonate backbones that will dissemble upon removal of protecting groups that can be used with the instant invention.

Materials with polymeric backbones are synthesized wherein the backbones have been molecularly engineered to incorporate units capable of absorbing multi-photon radiation simultaneously and initiating a cascade of changes within the higher order assembly. FIG. 30 depicts three such polymers based on a polyester and/or polycarbonate backbones that will disassemble upon deprotection of the hydroxyl protecting group and thus may be used with the methods and compounds of the present invention.

EXAMPLE 10

Nanoparticles of the present invention are synthesized in the presence of stem cell differentiation agents. They are administered to a patient in need of such treatment and disrupted in the immediate vicinity of an organ that has failed or is performing sub-optimally and is in need of stem cell therapy.

EXAMPLE 11

Nanoparticles of the present invention are loaded with non-infectious viral particles, DNA associated with a viral infection or associated with a disease, proteins associated with a viral infection or associated with a disease, and/or adjuvants. They are used to optimize cytotoxic T lymphocyte responses and antibody responses by sequestering vaccine and/or immunogen components until they reach a location within a patient's body where the components will produce their maximum effect. They are released at that location according to the methods of the present invention.

EXAMPLE 12

A combination of nanoparticles are synthesized according to the present invention the Payload(s) in one set comprises a luminescent enzyme and the Payload(s) in the other set comprises the enzyme's substrate. A small number of multi-photon absorption events results in a significant burst of luminescence as the enzyme and substrate are united.

EXAMPLE 13

Nanoparticles are synthesized according to the present invention where Payload(s) comprises antibodies. Multi-photon absorption events can releases multiple antibodies capable of binding multiple antigens at the point of release.

EXAMPLE 14

Encapsulation of viral particles, DNA, proteins, and adjuvants, in the same nanocarrier may help to realize optimal cytotoxic T lymphocytes (CTLs) responses and antibody responses by sequestering the vaccine components until they reach the target cell, delivering them to a particular class of cells, and/or aiding in their presentation via the desired pathway. One disease where the treatment will benefit from such technology is Herpes Simplex Virus-2.

HSV-2 causes a lifelong, persistent infection resulting in recurrent genital lesions. Transmission of the virus at birth also can cause devastating disease in the newborn. Of greatest importance worldwide, particularly in developing countries, is that genital HSV-2 infection significantly increases the risk of acquisition and transmission of HIV-1. Although antivirals are available, the lifelong persistence of this virus provides a strong impetus for the development of an effective vaccine.

Viral components included in a nanoparticle synthesized according to the present invention will include whole-inactivated virus as well as DNA plasmids encoding three specific HSV-2 genes. The first benefit of this approach is that whole-inactivated virus generates broader neutralizing antibody responses than single HSV-2 glycoprotein D subunit currently in vaccine trials. The DNA plasmids will comprise the HSV-2 gene encoding glycoprotein D as well as two genes that are highly conserved essential viral nonstructural proteins, viral DNA polymerase and helicase/primase. These genes will be excellent targets in infected cells for "primed" CD8 or CD4 T cells since immunization with the DNA will also generate CD4 and CD8 T-cell responses. Delivery of these antigens by DNA in the nanoparticle of the present invention, should bypass viral immunoevasive mechanisms, and the high T cell responses elicited may provide improved immunity over the natural infection.

A nanocarrier may be developed from acetalated-dextran containing DNA plasmids encoding HSV-2 glycoprotein D, DNA polymerase, and helicase/primase genes; formalin-inactivated HSV-2 virions; and an adjuvant such as MPL. Acetalated-dextran may be used in the Double Emulsion Condensation method to entrap different combinations of DNA plasmids and formalin-inactivated HSV-2 together with the adjuvant. The protective and immunological responses for each nanocarrier vaccine payload will be assessed.

Methods

BALB/c female mice will be immunized by subcutaneous injection twice, on weeks 0 and 4, with nanoparticle vaccines prepared according to the present invention or glycoprotein D subunit/MPL/alum vaccine, and then injected subcutaneously with 3 mg of medroxyprogesterone acetate (Depo-Provera) on days 21 and 27 after the last immunization to synchronize the estrus cycle and to increase susceptibility to vaginal HSV infection; on day 28, mice will be intravaginally challenged with 10×LD50 of HSV-2 strain G. Mice will be scored daily for 21 days for the severity of vaginal inflammation from 0 (no vaginitis), 1 (mild swelling or redness only), 2 (moderate swelling or erosions), 3 (severe genital maceration), or 4 (central nervous system involvement or death). Vaginal swab samples will be collected on days 1 to 7 post challenge to confirm viral replication and measure shedding. To evaluate immune responses, 3 weeks after the first and second immunization, several mice in each group will be bled and then sacrificed for isolation of splenocytes to determine levels of antibodies and primary T cell subsets, respectively, elicited. At 5 days after challenge, several mice in each group will be sacrificed to measure the recall responses.

Positive results from the BALB/c mouse tests will be more rigorously evaluated and compared with the HSV-2 glycoprotein D subunit/MPL/alum vaccine in the guinea pig model of genital HSV-2 infection. Guinea pigs develop external genital lesions that can be graded according to severity and are analogous to humans, in that the virus reactivates causing recurrent genital lesions.

Female Hartley guinea pigs will be immunized by bilateral injection in the quadriceps (4 weeks apart) with the optimal nanoparticle combinations or with HSV-2 glycoprotein D in MPL/alum. Four weeks after the last boost, anesthetized guinea pigs will be intravaginally challenged with 5.7 log 10 PFU of HSV-2 strain G. Animals will be scored daily for lesion development based on a severity scale of 0) no disease, 0.5) slight erythema/swelling only. 1) erythema/swelling only, 2) single or a few small lesions, 3) large or fused vesicles, and 4) ulcerated lesions. Viral shedding in the vagina will be measured on days 2, 5, 7, and 10 postchallenge and recurrence of vaginal disease will be assessed through day 90 postchallenge. At the conclusion of the experiment. DNA will be purified from the lumbrosacral ganglia from each guinea pig and used for real-time PCR quantification of latent HSV-2 DNA.

EXAMPLE 15

A polymer bearing boronic esters, shown in FIG. 21, was synthesized. Such a compound is sensitive to hydrogen peroxide. Cleavage of this polymer by hydrogen peroxide was demonstrated. Higher hydrogen peroxide concentrations in vivo are known to be associated with inflammatory and cardiovascular diseases.

Nanoparticles and microparticles of these polymers will be formulated and their efficacy in a variety of biomedical applications will be demonstrated.

Thus, embodiments of the present invention exist wherein the multi-photon responsive element may be replaced by a hydrogen peroxide responsive element.

The invention claimed is:

1. A method for delivering a Payload to a tissue comprising the steps of:

synthesizing a particle comprising polymer strands and a crosslinker to form a molecular network that encapsulates the Payload, wherein said crosslinker comprises a multi-photon responsive element covalently linked to a self-immolative backbone subunit comprising the structure where "PG" denotes a protecting group;

administering said particle to said tissue; and irradiating said tissue comprising said particle with electromagnetic radiation;

wherein said particle is disrupted in situ following absorption of said electromagnetic radiation.

2. The method of claim 1, wherein said electromagnetic radiation is near infrared red light or ultraviolet light.

3. The method of claim 1, wherein said method provides an amplified response to said electromagnetic radiation.

4. The method of claim 1, wherein said Payload comprises a pharmaceutical agent, stem cell differentiation agents, immunogens or antibodies.

5. The method of claim 1, wherein said multi-photon responsive element is a two-photon responsive element.

6. The method of claim 1, wherein said multi-photon responsive unit is a bromo-coumarin group.

7. The method of claim 1, wherein said molecular network comprises acrylamide polymers.

8. The method of claim 1, wherein said molecular network comprises PEG polymers.

9. The method of claim 1, wherein said self-immolative backbone subunit is a self-immolative dendrimer oligomer.

10. The method of claim 1, wherein said multi-photon responsive unit comprises the structure

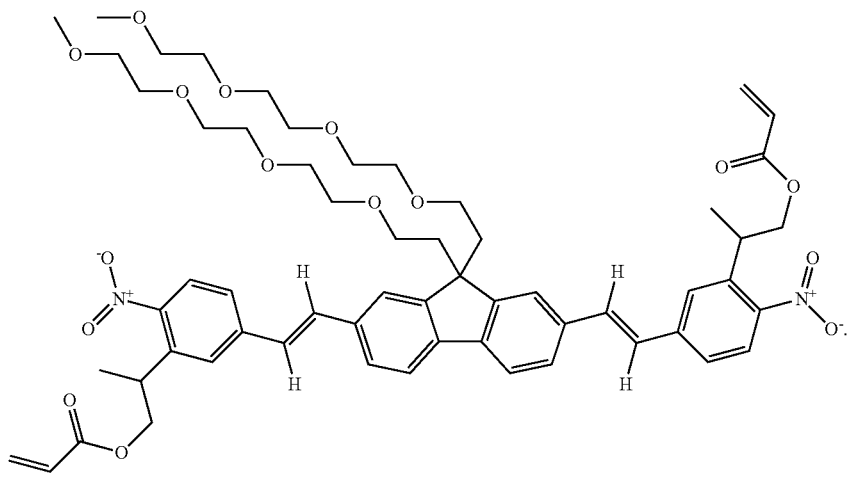

11. A method for delivering a Payload to a target tissue comprising:
encapsulating the Payload within a plurality of nanocarriers, each nanocarrier comprising a molecular cage synthesized by cross-linking polymer strands with a multi-photon responsive element covalently linked to a self-immolative backbone subunit comprising the structure

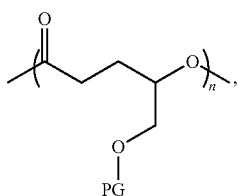

where "PG" denotes a protecting group;
administering said plurality of nanocarriers to said target tissue; and
irradiating said target tissue and the plurality of nanocarriers with electromagnetic radiation;
wherein said molecular cage unravels and releases the Payload in situ following absorption of said electromagnetic radiation.

12. The method of claim 11, wherein said electromagnetic radiation is near infrared red light or ultraviolet light.

13. The method of claim 11, wherein said Payload comprises a pharmaceutical agent, stem cell differentiation agents, immunogens or antibodies.

14. The method of claim 11, wherein said multi-photon responsive element is a two-photon responsive element.

15. The method of claim 11, wherein said polymer strands comprise polyacrylamide polymers.

16. A method for delivering a Payload to a target tissue comprising:
encapsulating the Payload within a molecular network comprising strands of polymer crosslinked by a crosslinker to form a carrier that mechanically encapsulates the Payload, the crosslinker comprising a dual-photon responsive element covalently linked to a self-immolative backbone subunit comprising the structure

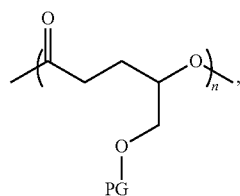

where "PG" denotes a protecting group;
administering a plurality of said carriers to said target tissue; and
irradiating said target tissue and said carriers with a dual-photon trigger;
wherein, upon exposure to the dual-photon trigger, the crosslinker cleaves to unravel the strands and release the Payload in situ.

17. The method of claim 16, wherein said electromagnetic radiation is near infrared red light or ultraviolet light.

18. The method of claim 16, wherein said Payload comprises a pharmaceutical agent, stem cell differentiation agents, immunogens or antibodies.

* * * * *